US010393500B2

(12) United States Patent
Yamauchi et al.

(10) Patent No.: US 10,393,500 B2
(45) Date of Patent: Aug. 27, 2019

(54) INTERFERENCE OBSERVATION DEVICE AND INTERFERENCE OBSERVATION METHOD

(71) Applicant: HAMAMATSU PHOTONICS K.K., Hamamatsu-shi, Shizuoka (JP)

(72) Inventors: Toyohiko Yamauchi, Hamamatsu (JP); Hidenao Yamada, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/546,168

(22) PCT Filed: Dec. 14, 2015

(86) PCT No.: PCT/JP2015/084919
§ 371 (c)(1),
(2) Date: Jul. 25, 2017

(87) PCT Pub. No.: WO2016/121250
PCT Pub. Date: Aug. 4, 2016

(65) Prior Publication Data
US 2018/0017371 A1    Jan. 18, 2018

(30) Foreign Application Priority Data

Jan. 30, 2015    (JP) ................. 2015-016266

(51) Int. Cl.
*G01B 9/02*    (2006.01)
*G01N 21/45*    (2006.01)
(Continued)

(52) U.S. Cl.
CPC ....... *G01B 9/0203* (2013.01); *G01B 9/02015* (2013.01); *G01B 9/02049* (2013.01);
(Continued)

(58) Field of Classification Search
CPC ............ G01B 9/02042; G01B 9/02056; G01B 9/02064; G01B 9/02067; G01B 9/02069; G01B 9/02071; G01B 9/0203
See application file for complete search history.

(56) References Cited

U.S. PATENT DOCUMENTS

| 5,847,827 A | 12/1998 | Fercher |
| 7,812,959 B1 | 10/2010 | Kim |

(Continued)

FOREIGN PATENT DOCUMENTS

| CN | 1623085 A | 6/2005 |
| CN | 1826518 A | 8/2006 |

(Continued)

OTHER PUBLICATIONS

Christopher Fang-Yen, et al, "Imaging voltage-dependent cell motions with heterodyne Mach-Zehnder phase microscopy", Optics Letters, vol. 32, No. 11, 2007, p. 1572-p. 1574.

(Continued)

*Primary Examiner* — Jonathan M Hansen
(74) *Attorney, Agent, or Firm* — Drinker Biddle & Reath LLP

(57) ABSTRACT

An interference observation apparatus includes a light source which outputs incoherent light, a beam splitter, a sample holding table, an objective lens, a reference mirror, a lens, an aberration correction plate, a piezo element, a tube lens, a beam splitter, an imaging unit, a photodetector, an image acquisition unit, and a control unit. The control unit obtains an interference intensity of combined light on the basis of a detection signal output from the photodetector, and adjusts an interference optical system to increase the interference intensity.

20 Claims, 23 Drawing Sheets

(51) Int. Cl.
    *G02B 21/00*     (2006.01)
    *G01N 33/483*     (2006.01)
    *G02B 21/06*     (2006.01)
    *G02B 21/36*     (2006.01)

(52) U.S. Cl.
    CPC ......... *G01N 21/45* (2013.01); *G01N 33/4833* (2013.01); *G02B 21/00* (2013.01); *G02B 21/06* (2013.01); *G02B 21/361* (2013.01); *G01B 9/02042* (2013.01)

(56) References Cited

U.S. PATENT DOCUMENTS

| | | | | |
|---|---|---|---|---|
| 8,248,593 | B2* | 8/2012 | Yamauchi | G01B 11/2441 356/237.2 |
| 2002/0196450 | A1* | 12/2002 | Olszak | G01B 11/2441 356/511 |
| 2005/0105097 | A1* | 5/2005 | Fang-Yen | G01B 9/02072 356/497 |
| 2009/0073450 | A1 | 3/2009 | Boyd et al. | |
| 2010/0309479 | A1* | 12/2010 | Yamauchi | G01B 11/2441 356/498 |

FOREIGN PATENT DOCUMENTS

| | | |
|---|---|---|
| CN | 101033937 A | 9/2007 |
| CN | 101313196 A | 11/2008 |
| CN | 103998969 A | 8/2014 |
| JP | S61-158311 A | 7/1986 |
| JP | H05-79815 A | 3/1993 |
| JP | H10-232204 A | 9/1998 |
| JP | 2001-4538 A | 1/2001 |
| JP | 2005-091165 A | 4/2005 |
| JP | 2005-345288 A | 12/2005 |
| JP | 4132308 B2 | 8/2008 |
| JP | 2009-116082 A | 5/2009 |
| JP | 2010-139326 A | 6/2010 |
| JP | 2012-132838 A | 7/2012 |
| JP | 2015-503128 A | 1/2015 |
| WO | WO-2013/095282 A2 | 6/2013 |

OTHER PUBLICATIONS

A. A. Freschi, et al, "Adjustable phase control in stabilized interferometry", Optics Letters, vol. 20, No. 6, 1995, p. 635-p. 637.

Pinhas Girshovitz, et al, "Generalized cell morphological parameters based on interferometric phase microscopy and their application to cell life cycle characterization", Biomedical Optics Express, vol. 3, No. 8, 2012, p. 1757-p. 1773.

Hidenao Iwai, et al, "Quantitative phase imaging using actively stabilized phase-shifting low-coherence interferometry", Optics Letters, vol. 29, No. 20, 2004, p. 2399-p. 2401.

Gordon S. Kino, et al, "Mirau correlation microscope", Applied Optics, vol. 29, No. 26, 1990, p. 3775-p. 3783.

Christopher J. Mann, et al, "High-resolution quantitative phasecontrast microscopy by digital holography", Optics Express, vol. 13, No. 22, 2005, p. 8693-p. 8698.

Lluis Martinez-Leon, et al, "Applications of short-coherence digital holography in microscopy", Applied Optics, vol. 44, No. 19, 2005, p. 3977-p. 3984.

Michael B. Sinclair, et al, "Long-working-distance incoherent-light interference microscope", Applied Optics, vol. 44, No. 36, 2005, p. 7714-p. 7721.

Ichirou Yamaguchi, et al, "Active phase-shifting interferometers for shape and deformation measurements", Opt. Eng., vol. 35, No. 10, 1996, p. 2930-p. 2937.

Toyohiko Yamauchi, et al, "Low-coherent quantitative phase microscope for nanometer-scale measurement of living cells morphology", Optics Express, vol. 16, No. 16, 2008, p. 12227-p. 12238.

Tong Zhang, et al, "Three-dimensional microscopy with phaseshifting digital holography", Optics Letters, vol. 23, No. 15, 1998, p. 1221-p. 1223.

International Preliminary Report on Patentability dated Aug. 10, 2017 for PCT/JP2015/084917.

International Preliminary Report on Patentability dated Aug. 10, 2017 for PCT/JP2015/084919.

* cited by examiner (a)

(b)

(a)

(b)

(a)

(b)

(a)

(b)

(a)

(b)

(a)

(b)

(a)

(b)

INTERFERENCE OBSERVATION DEVICE AND INTERFERENCE OBSERVATION METHOD

TECHNICAL FIELD

The present invention relates to an interference observation apparatus and an interference observation method.

BACKGROUND ART

An interference observation apparatus for acquiring an interference image causes light reflected by or transmitted through an observation object and reference light to interfere with each other using an optical system of a Michelson interferometer or a Mach-Zehnder interferometer, so that an interference image of the observation object can be acquired.

The interference observation apparatuses disclosed or suggested in Non Patent Documents 1 to 5 use an optical system of the Michelson interferometer, split light output from a light source into first split light and second split light, reflect the first split light by the observation object, and combine the first split light and the second split light. Then, the interference observation apparatuses acquire an image of interference light which is generated by the combining.

Among them, the interference observation apparatuses disclosed in Non Patent Documents 1 and 2 acquire the interference image using the light source (for example, a halogen lamp or an LED (Light Emitting Diode)) which outputs incoherent light. The interference observation apparatuses disclosed or suggested in Non Patent Documents 3 and 4 acquire the interference image using the light source which outputs coherent laser light, and perform feedback control on an optical path difference between two optical paths in the Michelson interferometer on the basis of a detection result of the interference light.

The interference observation apparatus disclosed in Non Patent Document 5 acquires the interference image using a first light source which outputs incoherent light, and performs feedback control on an optical path difference between two optical paths in the Michelson interferometer on the basis of a detection result of the interference light and using a second light source which outputs coherent laser light.

The interference observation apparatuses disclosed in Non Patent Documents 7 to 11 split light output from a light source using an optical system of the Mach-Zehnder interferometer into first split light and second split light, and transmit or reflect the first split light by the observation object, and combine the first split light and the second split light. Then, the interference observation apparatuses acquire an image of interference light which is generated by the combining.

Among them, the interference observation apparatuses disclosed in Non Patent Documents 7 to 9, and 11 use the light source which outputs coherent laser light. Further, the interference observation apparatus disclosed in Non Patent Document 10 uses the light source which outputs temporally incoherent light. The interference observation apparatuses of Non Patent Documents 7 to 9 do not include a function of adjusting the optical path difference between two optical paths in the Mach-Zehnder interferometer. On the other hand, the interference observation apparatuses of Non Patent Documents 10 and 11 include the function of adjusting the optical path difference.

Here, a technique of keeping the optical path difference constant between two optical paths in the interferometer by the feedback control on the basis of the interference light detection result is called "phase lock". A technique of changing a value of the optical path difference kept by the phase lock using the feedback control is called "phase shift".

CITATION LIST

Non Patent Literature

Non Patent Document 1: Gordon S. Kino, et al, "Mirau correlation microscope," APPLIED OPTICS, Vol. 29, No. 26, pp. 3775-3783 (1990).

Non Patent Document 2: Michael B. Sinclair, et al, "Long-working-distance incoherent-light interference microscope," APPLIED OPTICS, Vol. 44, No. 36, pp. 7714-7721 (2005).

Non Patent Document 3: A. A. Freschi, et al, "Adjustable phase control in stabilized interferometry," OPTICS LETTERS, Vol. 20, No. 6, pp. 635-637 (1995).

Non Patent Document 4: Ichirou Yamaguchi, et al, "Active phase-shifting interferometers for shape and deformation measurements," Opt. Eng., Vol. 35, No. 10, pp. 2930-2937 (1996).

Non Patent Document 5: Toyohiko Yamauchi, et al, "Low-coherent quantitative phase microscope for nanometer-scale measurement of living cells morphology," OPTICS EXPRESS, Vol. 16, No. 16, pp. 12227-12238 (2008).

Non Patent Document 6: Hidenao Iwai, et al, "Quantitative phase imaging using actively stabilized phase-shifting low-coherence interferometry," OPTICS LETTERS, Vol. 29, No. 20, pp. 3299-2401 (2004).

Non Patent Document 7: Tong Zhang, et al, "Three-dimensional microscopy with phase-shifting digital holography," OPTICS LETTERS, Vol. 23, No. 15, pp. 1221-1223 (1998).

Non Patent Document 8: Christopher Fang-Yen, et al, "Imaging voltage-dependent cell motions with heterodyne Mach-Zehnder phase microscopy," OPTICS LETTERS, Vol. 32, No. 11, pp. 1572-1574 (2007).

Non Patent Document 9: Christopher J. Mann, et al, "High-resolution quantitative phase-contrast microscopy by digital holography," OPTICS EXPRESS, Vol. 13, No. 22, pp. 8693-8698 (2005).

Non Patent Document 10: Lluis Martinez-Leon, et al, "Applications of short-coherence digital holography in microscopy," APPLIED OPTICS, Vol. 44, No. 19, pp. 3977-3984 (2005).

Non Patent Document 11: Pinhas Girshovitz, et al, "Generalized cell morphological parameters based on interferometric phase microscopy and their application to cell life cycle characterization," BIOMEDICAL OPTICS EXPRESS, Vol. 3, No. 8, pp. 1757-1773 (2012).

SUMMARY OF INVENTION

Technical Problem

An interference observation apparatus having no phase lock function hardly acquires the interference image which is quantitatively excellent. In order to acquire the quantitatively excellent interference image using the interference observation apparatus having no phase lock function, it is considered that the phase shift is performed at a speed higher than mechanical noises caused from an environment, and the interference image is acquired using a high-speed camera. However, in this case, an expensive high-speed piezo stage and an expensive high-speed camera are necessary, and therefore, the interference observation apparatus becomes also expensive. Further, in this case, the exposure time of the camera is short, and therefore, power of the light output from the light source has to be increased. In a case where a biological sample which is weak in light is used as an observation object, it is not preferable to irradiate the observation object with such high intensity light.

An interference observation apparatus which acquires the interference image and performs the phase lock on the basis of a detection result of the interference light using laser light output from a laser light source can acquire the quantitatively excellent interference image. However, the interference image acquired by this interference observation apparatus is degraded in image quality by interference noises which are represented by speckle noises. That is, high coherent light such as laser light interferes regardless of the optical path difference between two optical paths in the interferometer, and thus the optical adjustment is easily made, however, light passing through an undesired optical path (for example, light returning from the optical element provided on the path) also causes the interference at the same time. Therefore, diffraction noises are overlapped with the interference image. Further, it is known that noises are overlapped with an image in a speckle shape in the imaging using laser light.

As described above, in a case where incoherent light is used, the image quality of the interference image is good, however, the optical adjustment is hard. On the other hand, in a case where high coherent light is used, the optical adjustment is easily performed, however, the image quality of the interference image is degraded. There is a tradeoff between the image quality of the interference image and the easiness of the optical adjustment.

The interference observation apparatus disclosed in Non Patent Document 5 can acquire an interference image with a good image quality using the incoherent light, and can perform the phase lock and the phase shift using the laser light. However, since this interference observation apparatus includes two light sources, it becomes expensive. Further, since there is a need to exactly match the optical path of the incoherent light and the optical path of the laser light, and readjustment after assembling of the apparatus and conveyance requires a precise operation, and it is hard for a general user other than an expert of an optical system.

The present invention has been made in order to solve the above problem, and an object thereof is to provide an interference observation apparatus and an interference observation method which can easily acquire an interference image with a good image quality, and configure the apparatus at a low cost.

Solution to Problem

An interference observation apparatus according to one embodiment of the present invention is an apparatus for acquiring an interference image of an observation object, and includes (1) a light source for outputting incoherent light, (2) an interference optical system for splitting the light output from the light source into first split light and second split light, reflecting or transmitting the first split light by an observation object, and combining the first split light and the second split light to output combined light, (3) a light receiving unit for receiving the combined light and outputting a detection signal, (4) an image acquisition unit for acquiring an interference image on the basis of the detection signal, and (5) a control unit for obtaining an interference intensity of the combined light on the basis of the detection signal, and adjusting the interference optical system to increase the interference intensity.

An interference observation method according to one embodiment of the present invention is a method for acquiring an interference image of an observation object, and includes (1) splitting incoherent light output from a light source using an interference optical system into first split light and second split light, reflecting or transmitting the first split light by an observation object, and combining the first split light and the second split light to output combined light, (2) receiving the combined light using a light receiving unit and outputting a detection signal, (3) acquiring an interference image on the basis of the detection signal using an image acquisition unit, and (4) obtaining an interference intensity of the combined light on the basis of the detection signal, and adjusting the interference optical system to increase the interference intensity.

Advantageous Effects of Invention

According to the present invention, it is possible to easily acquire an interference image with a good image quality, and to configure the apparatus at a low cost.

DESCRIPTION OF EMBODIMENTS

Hereinafter, embodiments for carrying out the present invention will be described in detail with reference to the accompanying drawings. In the description of the drawings, the same or equivalent elements will be denoted by the same reference signs, without redundant description. The present invention is not limited to these examples, and the Claims, their equivalents, and all the changes within the scope are intended as would fall within the scope of the present invention.

First Embodiment

Figure 1:
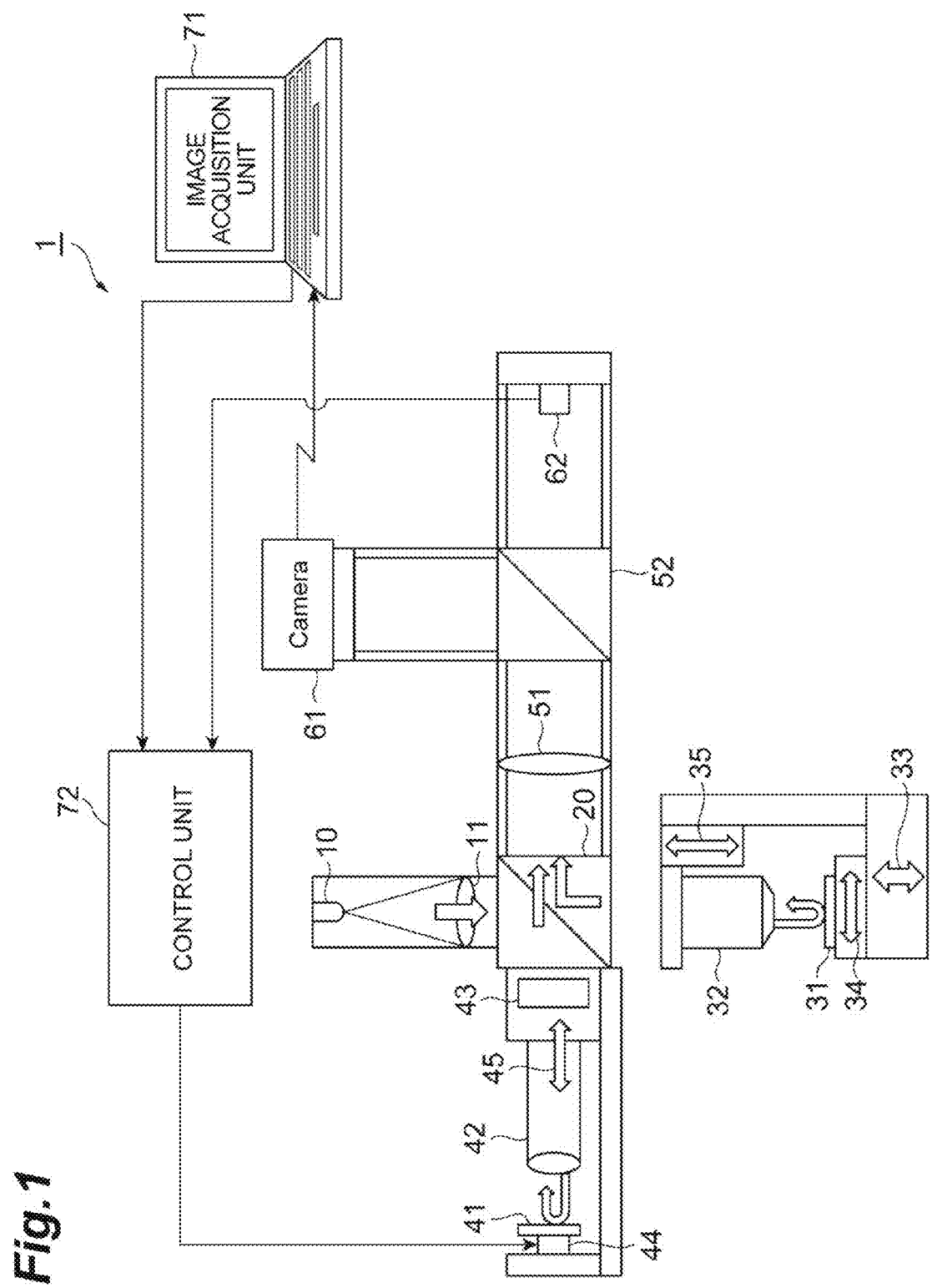
FIG. 1 is a diagram illustrating a configuration of an interference observation apparatus 1.

FIG. 1 is a diagram illustrating a configuration of an interference observation apparatus 1 of the first embodiment. The interference observation apparatus 1 includes a light source 10, a lens 11, a beam splitter 20, a sample holding table 31, an objective lens 32, stages 33 to 35, a reference mirror 41, a lens 42, an aberration correction plate 43, a piezo element 44, a stage 45, a tube lens 51, a beam splitter 52, an imaging unit 61, a photodetector 62, an image acquisition unit 71, and a control unit 72.

The interference observation apparatus 1 includes an optical system of the Michelson interferometer, and acquires an interference image on the basis of the light reflected by an observation object held on the sample holding table 31. The observation object is not limited to a specific cell or a biological sample. For example, the observation object includes a cultured cell, an immortalized cell, a primary cultured cell, a cancer cell, a fat cell, a liver cell, a cardiac muscle cell, a nerve cell, a glia cell, a somatic stem cell, an embryonic stem cell, a pluripotential stem cell, an iPS cell, and a cell aggregation (spheroid) created on the basis of at least one of these cells. Further, the observation object is not limited to a biological object, and includes an industrial sample such as a metal surface, a semiconductor surface, a glass surface, an inside of a semiconductor element, a resin material surface, a liquid crystal, and a high molecular compound.

The light source 10 outputs incoherent light. The light source 10 may be, for example, a lamp light source such as a halogen lamp, an LED (Light emitting diode) light source, an SLD (Super luminescent diode) light source, or an ASE (Amplified spontaneous emission) light source, or the like. The lens 11 collimates the light output from the light source 10.

The beam splitter 20 is optically coupled to the light source 10, and forms the optical system of the Michelson interferometer. The beam splitter 20 may be a half mirror for example. The beam splitter 20 splits the light collimated by the lens 11 into two components to form first split light and second split light. The beam splitter 20 outputs the first split light to the objective lens 32, and outputs the second split light to the aberration correction plate 43. Further, the beam splitter 20 inputs the first split light reflected by the observation object which is held on the sample holding table 31 and passing through the objective lens 32, inputs the second split light reflected by the reference mirror 41 and passing through the aberration correction plate 43, and combines the thus input first split light and the second split light to output the combined light to the lens 51.

The objective lens 32 is optically coupled to the beam splitter 20, and condenses the first split light output from the beam splitter 20 to the observation object held on the sample holding table 31. Further, the objective lens 32 inputs the first split light reflected by the observation object and outputs the light to the beam splitter 20. The stage 33 translates the sample holding table 31 in a direction parallel to an optical axis of the objective lens 32. The stage 34 translates the sample holding table 31 in two directions intersecting with the optical axis of the objective lens 32 (for example, two directions perpendicular to the optical axis of the objective lens 32). The stage 35 adjusts a distance between the objective lens 32 and the sample holding table 31.

The lens 42 is optically coupled to the beam splitter 20, and condenses the second split light output from die beam splitter 20 and passing through the aberration correction plate 43 to the reference mirror 41. Further, the lens 42 outputs the second split light reflected by the reference mirror 41 to the beam splitter 20 through the aberration correction plate 43. The piezo element 44 moves the reference mirror 41 in a direction parallel to an optical axis of the lens 42. The stage 45 roughly adjusts a distance between the reference mirror 41 and the lens 42.

The tube lens 51 is optically coupled to the beam splitter 20 forming the interference optical system, and forms an image of the combined light output from the beam splitter 20 on an imaging plane of the imaging unit 61 through the beam splitter 52. The beam splitter 52 is optically coupled to the beam splitter 20 forming the interference optical system, serves as a splitting unit which splits the light arrived from the lens 51, outputs one split light (first detection light) to the imaging unit 61, and outputs the other split light (second detection light) to the photodetector 62. The beam splitter 52 may be a half mirror for example.

A light receiving unit which receives the combined light and outputs a detection signal is optically coupled to the beam splitter 20 of the interference optical system, and includes the imaging unit 61 and the photodetector 62. The imaging unit 61 receives the first detection light arrived from the beam splitter 52 and outputs the received light signal (first detection signal). The imaging unit 61 is, for example, an image sensor such as a CCD area image sensor or a CMOS area image sensor. The photodetector 62 receives the second detection light arrived from the beam splitter 52 and outputs the received light signal (second detection signal). The photodetector 62 is, for example, a photodiode, an avalanche photodiode, a photomultiplier tube, a line sensor (linear sensor), a CCD area image sensor, or a CMOS area image sensor. The image acquisition unit (image processing device) 71 acquires the interference image on the basis of the first detection signal output from the imaging unit 61. The control unit (controller) 72 performs control on the basis of the second detection signal output from the photodetector 62.

Here, each of the image acquisition unit 71 and the control unit 72 is a computer which includes a processor and a memory. Further, the image acquisition unit 71 and the control unit 72 may be configured by individual computers, or may be configured by one computer. The computer may be, for example, a personal computer or a smart device such as a tablet terminal. Further, the image acquisition unit 71 or the control unit 72 may include an input unit (keyboard, mouse, tablet terminal, etc.) which receives an input from a user, and a display unit (display, tablet terminal, speaker, vibrator, etc.) which displays an interference intensity, etc. Further, in a case where the display unit can display a screen such as the display or the tablet terminal, the interference image etc. may be displayed with the interference intensity.

In the optical system on the sample side (the optical system of the first split light) and the optical system on the reference side (the optical system of the second split light), respectively, the lenses 32 and 42 are provided to form light images at reflection positions (the observation object, the reference mirror 41). In this way, the interference optical system in which the objective lens (or equivalent lens) is provided in both of optical systems is known as a Linnik-type interferometer. In the configuration illustrated in FIG. 1, an aspherical achromatic lens 42 reduced in size and in weight and the aberration correction plate 43 are used in place of the objective lens to achieve the reduction in weight of the optical system on the reference side (the optical system of the second split light).

The stage 33 is configured to move the sample holding table 31 in a direction of the optical axis of the objective lens 32, and can adjust the optical path length of the optical system on the sample side (the optical system of the first split light). The piezo element 44 is configured to move the reference mirror 41 in a direction of the optical axis of the lens 42, and can adjust the optical path length of the optical system on the reference side (the optical system of the second split light). In place of the piezo element 44, an actuator such as a stepping motor or a servo motor may be used. The stage 33 and the piezo element 44 can adjust a difference between the optical path length of the optical system on the sample side (the optical system of the first split light) and the optical path length of the optical system on the sample side (the optical system of the first split light), and operates as an optical path difference adjusting unit which adjusts the optical path difference between the first split light and the second split light from the splitting to the combining in the interference optical system. The control unit 72 controls an optical path difference adjusting operation by the optical path difference adjusting unit (the stage 33, the piezo element 44).

After being collimated by the lens 11, the incoherent light output from the light source 10 is split into two components by the beam splitter 20 to be the first split light and the second split light. The first split light is condensed by the objective lens 32 to the observation object which is held on the sample holding table 31, and reflected on the surface or the inner portion of the observation object. The reflected first split light is input to the beam splitter 20 through the objective lens 32. The first split light has an optical delay when the light is reflected by the observation object. The second split light is condensed by the lens 42 to the reference mirror 41 through the aberration correction plate 43, and reflected by the reference mirror 41. The reflected second split light is input to the beam splitter 20 through the lens 42 and the aberration correction plate 43.

The first split light input from the objective lens 32 to the beam splitter 20 and the second split light input from the tens 42 to the beam splitter 20 are combined by the beam splitter 20. The combined light is split into two components by the beam splitter 52 through the tube lens 51, received by the imaging unit 61, and received by the photodetector 62. The image acquisition unit 71 acquires the interference image on the basis of the first detection signal output from the imaging unit 61 which receives the combined light. Further, the control unit 72 controls the optical path difference adjusting operation by the optical path difference adjusting unit (the stage 33, the piezo element 44) on the basis of the second detection signal output from the photodetector 62 which receives the combined light.

In the configuration illustrated in FIG. 1, the observation object held on the sample holding table 31 and the objective lens 32 can integrally move in a direction of the optical axis of the objective lens 32 by the stage 33, and therefore, the optical path difference can be adjusted while keeping the respective imaging conditions of the objective lens 32 and the lens 42. Further, in interference observation apparatuses 1A to 1D of modifications illustrated in FIG. 2 to FIG. 5, the optical path difference can also be adjusted while keeping the respective imaging conditions of the objective lens 32 and the lens 42.

Figure 2:
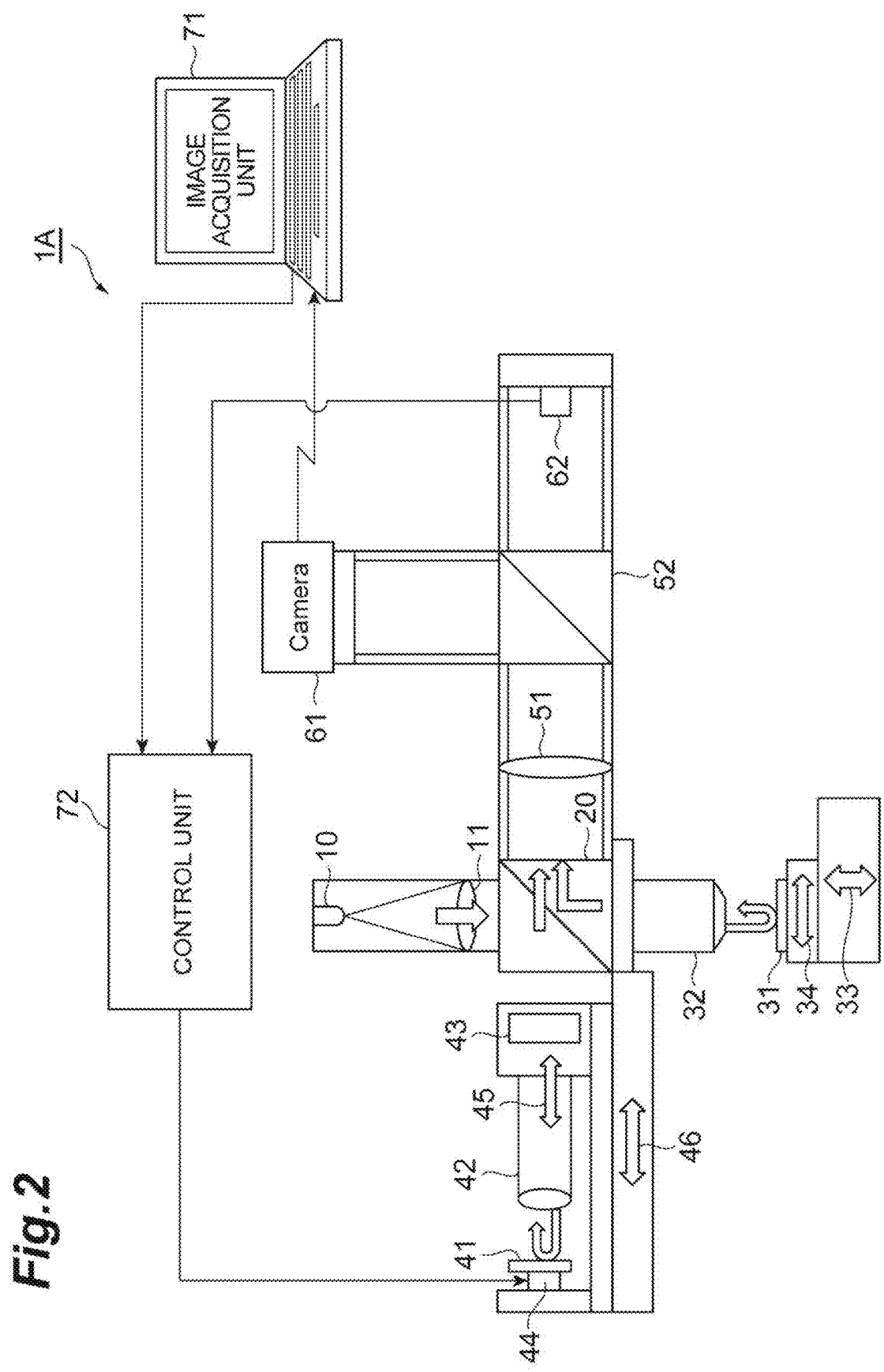
FIG. 2 is a diagram illustrating a configuration of an interference observation apparatus 1A.

The interference observation apparatus 1A of the modification illustrated in FIG. 2 is different from that of FIG. 1 in that the position of the objective lens 32 is fixed, and there is provided a stage 46 which integrally moves the reference mirror 41, the lens 42, and the aberration correction plate 43 in a direction of the optical axis of the lens 42.

Figure 3:
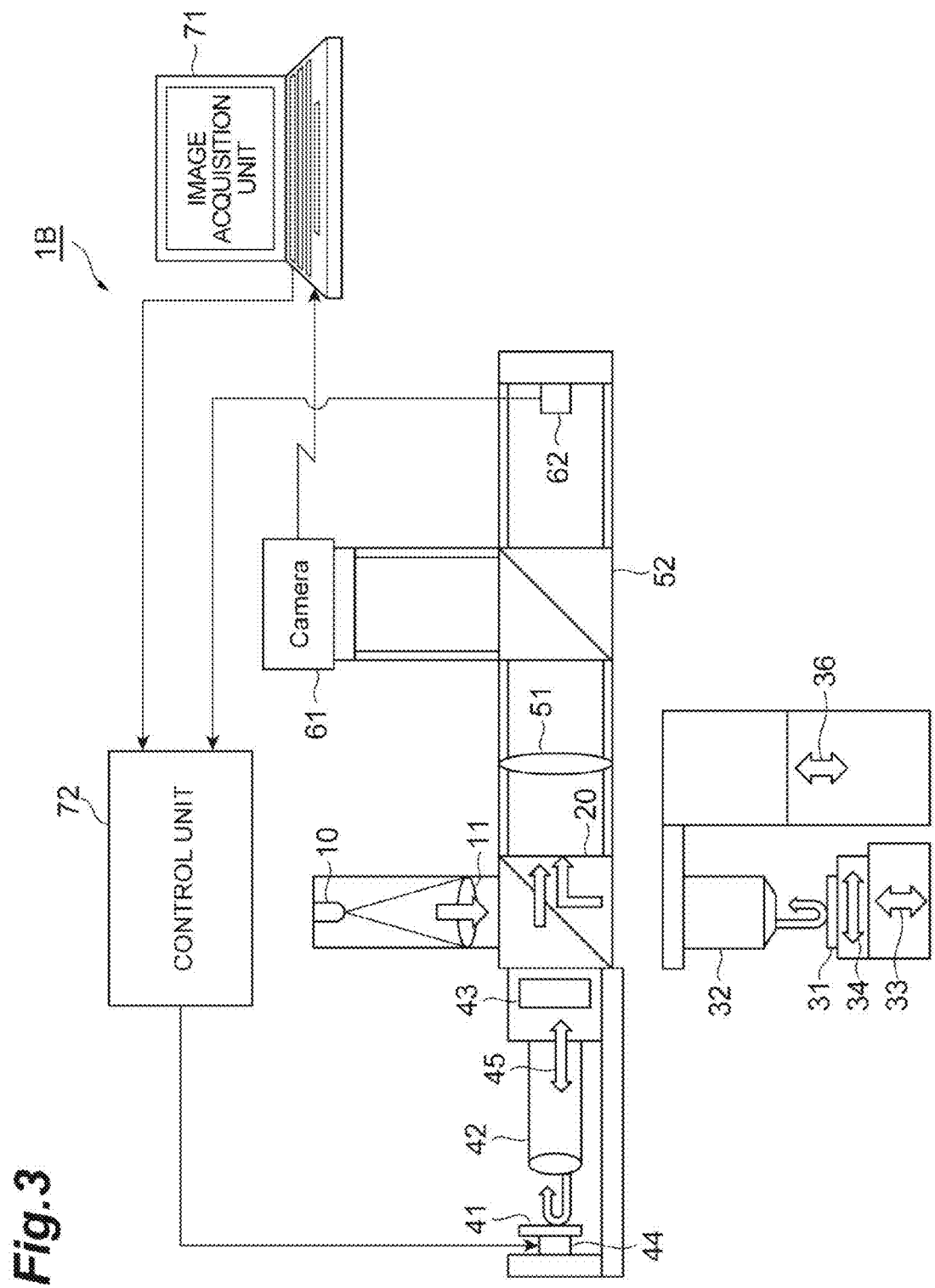
FIG. 3 is a diagram illustrating a configuration of an interference observation apparatus 1B.

The interference observation apparatus 1B of the modification illustrated in FIG. 3 is different from that of FIG. 1 in that there is provided a stage 36 which moves the objective lens 32 independently from the sample holding table 31 in a direction of the optical axis in place of the stage 35 which adjusts a distance between the sample holding table 31 and the objective lens 32. The interference observation apparatus 1B can adjust the optical path difference while keeping the respective imaging conditions of the objective lens 32 and the lens 42 by cooperatively controlling the stage 33 which moves the sample holding table 31 in a direction of the optical axis of the objective lens 32 and the stage 36 which moves the objective lens 32 in a direction of the optical axis.

Figure 4:
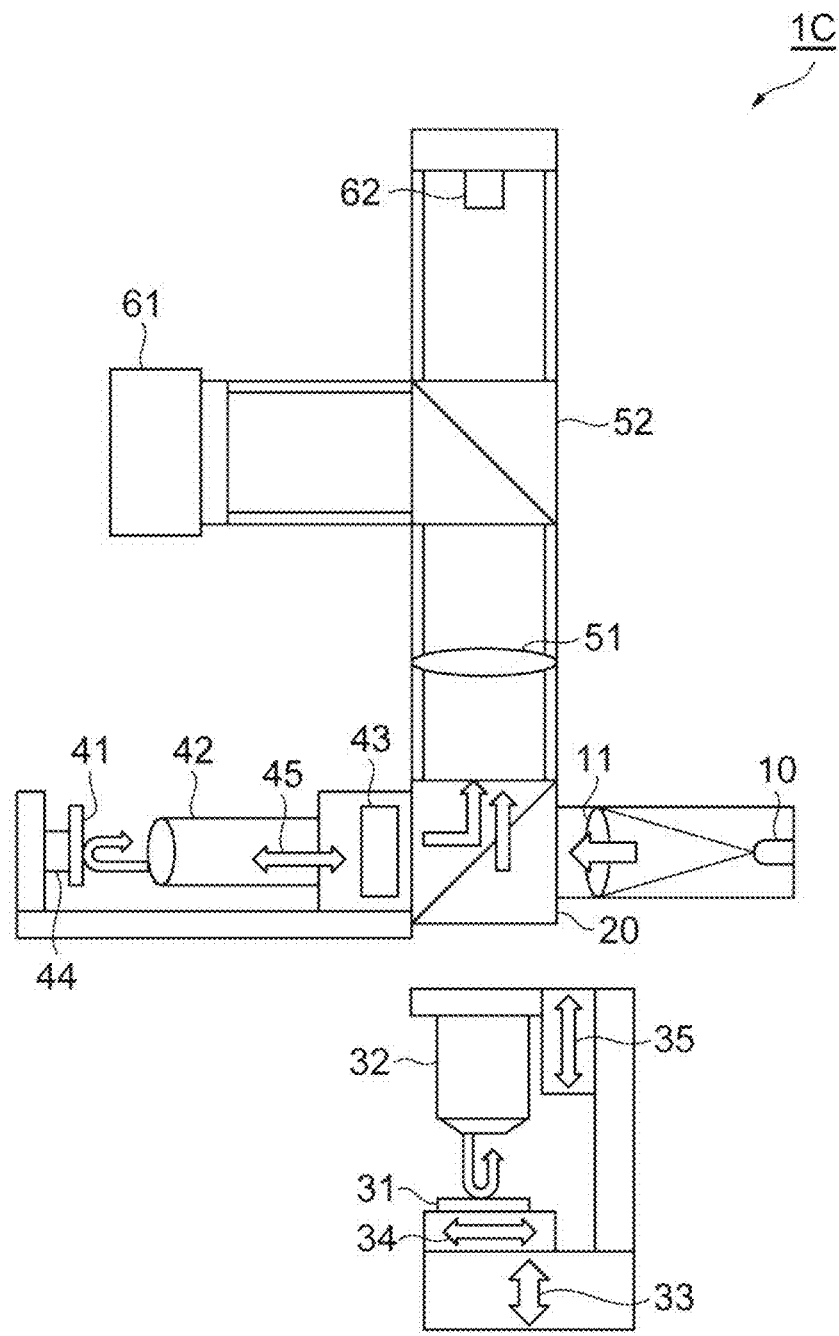
FIG. 4 is a diagram illustrating a configuration of an interference observation apparatus 1C.

The interference observation apparatus 1C of the modification illustrated in FIG. 4 is different from that of FIG. 1 in that the optical path from the light source 10 to the beam splitter 20 and the optical path from the beam splitter 20 to the imaging unit 61 and the photodetector 62 are switched.

Figure 5:
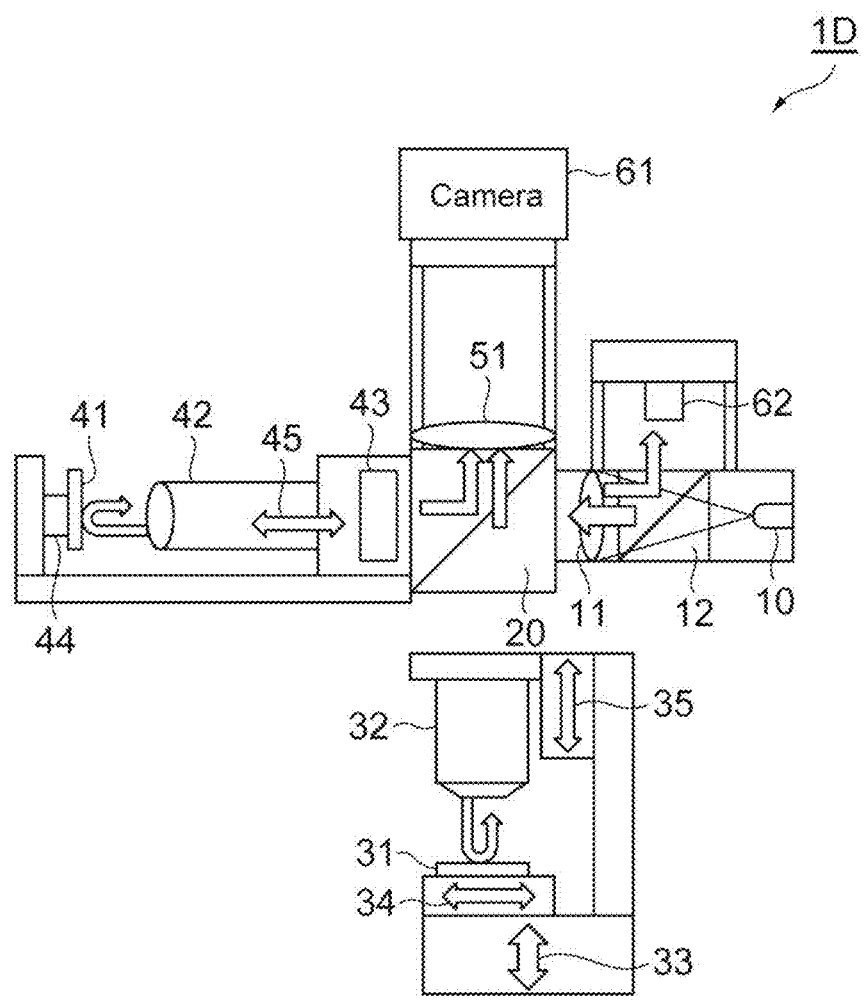
FIG. 5 is a diagram illustrating a configuration of an interference observation apparatus 1D.

The interference observation apparatus 1D of the modification illustrated in FIG. 5 is different from that of FIG. 1 in that a beam splitter 12 is provided in place of the beam splitter 52, and different in the position of the photodetector 62. The beam splitter 20 outputs the combined light to both the tube lens 51 and the lens 11. The beam splitter 12 is provided on the optical path between the light source 10 and the lens 11, reflects part of the combined light which is output from the beam splitter 20 and converged by the lens 11, and inputs the light to the photodetector 62.

In the present embodiment, since the interference image is acquired using the incoherent light output by the light source 10, there is a need to perform a phase lock and a phase shift by controlling the optical path difference. This is because, in the case of the incoherent light, that is, white light, the interference is obtained in a case where the optical path difference is a coherence length $\Delta L_C$ or less. When a center wavelength of the incoherent light is set to $\lambda_0$, and a spectrum width of the incoherent light is set to $\Delta\lambda$, the coherence length $\lambda L_C$ is expressed by the following Formula (1). In the case of an LED, the coherence length $\Delta L_C$ is about 10 μm. In the case of a halogen lamp, the coherence length $\Delta L_C$ is about 1 μm.

[Formula 1]

$$\Delta L_C = 2 \times 0.441 \frac{\lambda_0^2}{\Delta\lambda} \quad (1)$$

In the present embodiment, the control unit 72 controls the optical path difference adjusting operation by the optical path difference adjusting unit (the stage 33, the piezo element 44) on the basis of the detection signal output from the photodetector 62 which receives the combined light output from the beam splitter 52, and performs the phase lock and the phase shift.

Here, strictly speaking, the movement of the reference mirror 41 by the piezo element 44 causes an imaging condition in the reference optical system to be different. However, an actual scan distance of the reference mirror 41 is about a half of the wavelength of the light, and for example, in a case where a red LED (610 nm in wavelength) is used as the light source 10, the distance becomes about 305 nm. This movement amount is almost the same as a focal depth of the lens 42 (or the objective lens of an equivalent product) or a significantly short distance. Therefore, even when the reference mirror 41 is moved by the piezo element 44, it can be considered that the imaging condition in the optical system on the reference side is substantially kept.

In an actual experimental environment, it is not possible to avoid that the optical path length vibrates about 10 nm per 1 second on an experiment table with vibration countermeasure, and further, it is a common thing that the optical path length is disturbed by 100 nm or more per 1 second on an experiment table without vibration countermeasure. Accordingly, in a high-accuracy interference imaging, it is essential that the optical path difference is locked.

As the phase lock, a technique disclosed in Non Patent Documents 3, 5, and 6 may be used (hereinafter, referred to as "first phase lock technique"). In the phase lock technique disclosed in these Non Patent Documents, the reference minor 41 is caused to vibrate at a high speed in a sinusoidal manner with a sufficiently small amplitude compared to the wavelength of the output light of the light source 10, and at this time, the detection signal output from the photodetector 62 is detected in synchronization with one time and two times the vibration frequency of the reference mirror 41, to obtain the phase of the interference light. The control unit 72 performs feedback control to make the obtained phase value approach a target value, so that the optical path difference can be locked.

The control unit 72 inputs the detection signal which is an analog signal from the photodetector 62, and outputs an analog signal for the drive control of the stage 33 or the piezo element 44. The control unit 72 may perform an analog process internally, or a digital process. In the latter case, for example, the control unit 72 may perform an AD conversion on the input detection signal into a digital signal, process the digital signal, perform a DA conversion on the digital signal obtained by the processing to obtain an analog signal, and output the analog signal. In processing the digital signal, a microprocessor or an FPGA (Field Programmable Gate Array) may be used.

When a phase difference $\Delta\phi$ corresponding to the optical path difference is generated, an intensity V of the light received by the photodetector 62 is expressed by the following Formula (2). The light receiving intensity V includes an offset component DC and an amplitude AC which are all unknown. Therefore, there is a need to extract the phase difference $\Delta\phi$ where the DC and the AC are not contained by a certain process.

[Formula 2]

$$V = DC + AC \cdot \sin(\Delta\phi) \quad (2)$$

When the reference mirror 41 is caused to vibrate at a high speed in a sinusoidal manner by the piezo element 44 with a sufficiently small amplitude compared to the wavelength of the output light of the light source 10, the intensity V of the light received by the photodetector 62 is expressed by the following Formula (3). $\alpha$ is a modulation degree which is determined according to an amplitude of the vibration of the reference mirror 41. $\omega$ is an angular frequency of the vibration. t is a time variable.

[Formula 3]

$$V(t) = DC + AC \cdot \sin(\Delta\phi + \alpha \cdot \sin(\omega t)) \quad (3)$$

When the right side of Formula (3) is expanded in a Fourier series, the following Formula (4) is obtained as an approximation formula. $J_1$ and $J_2$ are Bessel functions of the first kind. The second term in the right side of Formula (4a) vibrates at an amplitude $A_{\omega t}$ and an angular frequency $\omega$. Further, the third term in the right side of Formula (4a) vibrates at an amplitude $A_{2\omega t}$ and an angular frequency $2\omega$. Therefore, the detection signal output from the photodetector 62 is synchronously detected with the angular frequency $\omega$ to obtain the amplitude $A_{\omega t}$, and the detection signal is synchronously detected with the angular frequency $2\omega$ to obtain the amplitude $A_{2\omega t}$.

[Formula 4]

$$V(t) = DC' + A_{\omega t} \sin(\omega t) + A_{2\omega t} \cos(2\omega t) + \ldots \quad (4a)$$

$$A_{\omega t} = 2 \cdot AC \cdot J_1(\alpha) \cdot \cos(\Delta\phi) \quad (4b)$$

$$A_{2\omega t} = 2 \cdot AC \cdot J_2(\alpha) \cdot \sin(\Delta\phi) \quad (4c)$$

A ratio of the amplitude $A_{\omega t}$ and the amplitude $A_{2\omega t}$ is expressed by the following Formula (5). Further, the AC indicates the interference intensity of the combined light, and the interference intensity AC is expressed by the following Formula (6). Since the amplitude of the vibration of the reference mirror 41 is constant, $J_1(\alpha)$ and $J_2(\alpha)$ can be obtained on the basis of the amplitude. The phase difference $\Delta\phi$ in accordance with the optical path difference can be obtained on the basis of Formula (5), and the interference intensity AC can be obtained on the basis of Formula (6). The control unit 72 includes a synchronous detection circuit, an adding circuit, and a multiplying and dividing circuit for performing the above processes.

[Formula 5]

$$\frac{A_{2\omega t}}{A_{\omega t}} = \frac{2 \cdot AC \cdot J_2(\alpha) \cdot \sin(\Delta\phi)}{2 \cdot AC \cdot J_1(\alpha) \cdot \cos(\Delta\phi)} = \frac{J_2(\alpha)}{J_1(\alpha)} \tan(\Delta\phi) \quad (5)$$

[Formula 6]

$$AC^2 = \left(\frac{A_{\omega t}}{2 \cdot J_1(\alpha)}\right)^2 + \left(\frac{A_{2\omega t}}{2 \cdot J_2(\alpha)}\right)^2 \quad (6)$$

The present embodiment performs the phase lock using the incoherent light. Conventionally, the coherence of the incoherent light is low, and thus it has been difficult to use the incoherent light in the phase lock. However, in the present embodiment, it is possible to urge an operator to optimize an interference state in the optical system by obtaining the interference intensity AC of the incoherent light. That is, when the optical path difference in the interferometer is sufficiently large compared to the coherence length of the light, the interference intensity AC approaches zero. When the optical path difference in the interferometer is zero, the interference intensity AC becomes a maximum value. The interference intensity AC is obtained to adjust the optical path difference for increasing the interference intensity AC.

The phase lock technique (hereinafter, referred to as "second phase lock technique") using a "spatial filtering detector" disclosed in Non Patent Document 4 can also be used. In this technique, a line sensor having a plurality of pixels arranged in one-dimensional direction or a plurality of photodetectors arranged in one-dimensional direction is used in place of the photodetector 62. In the following, the description will be given about a case where four photodetectors arranged at equal intervals are used. An inclination is given to both or any one of the optical system on the measurement side and the optical system on the reference side to make interference fringes appear, and in this state, the inclination of the interference fringes is adjusted to set the light receiving intensities $V_1$ to $V_4$ of the four photodetectors to be obtained as the following Formula (7).

[Formula 7]

$$V_1 = DC + AC \cdot \sin(\Delta\phi) \quad (7a)$$

$$V_2 = DC + AC \cdot \sin(\Delta\phi + \pi/2) = DC - AC \cdot \cos(\Delta\phi) \quad (7b)$$

$$V_3 = DC + AC \cdot \sin(\Delta\phi + \pi) = DC - AC \cdot \sin(\Delta\phi) \quad (7c)$$

$$V_4 = DC + AC \cdot \sin(\Delta\phi + 3\pi/2) = DC - AC \cdot \cos(\Delta\phi) \quad (7d)$$

For applying an inclination to both or any one of the optical system on the measurement side and the optical system on the reference side, for example, the sample holding table 31 or the reference mirror 41 may be inclined, or any one of the lenses may be inclined, or a wedge-shaped prism having different thicknesses along a predetermined direction may be inserted on the optical path.

$A_1$ and $A_2$ are obtained from the light receiving intensities $V_1$ to $V_4$ by the following Formula (8), and a ratio of $A_1$ and $A_2$ is obtained by the following Formula (9). Further, the interference intensity AC is expressed by the following Formula (10). From these Formulas, the phase difference $\Delta\phi$ in accordance with the optical path difference can be obtained, and the interference intensity AC can also be obtained. The control unit 72 may realize the above processes by a simple electric circuit.

[Formula 8]

$$A_1 = V_1 - V_3 = 2 \cdot AC \cdot \sin(\Delta\phi) \quad (8a)$$

$$A_2 = V_4 - V_2 = 2 \cdot AC \cdot \cos(\Delta\phi) \quad (8b)$$

[Formula 9]

$$\frac{A_1}{A_2} = \frac{2 \cdot AC \cdot \sin(\Delta\phi)}{2 \cdot AC \cdot \cos(\Delta\phi)} = \tan(\Delta\phi) \quad (9)$$

[Formula 10]

$$AC^2 = \left(\frac{A_1}{2}\right)^2 + \left(\frac{A_2}{2}\right)^2 \quad (10)$$

In this way, the control unit 72 obtains the phase difference in accordance with the optical path difference and also obtains the interference intensity, controls the optical path difference adjusting operation by the optical path difference adjusting unit (the stage 33, the piezo element 44), so that the optical path difference is made small on the basis of the obtained interference intensity, and the optical path difference is kept constant on the basis of the obtained phase difference. Further, when the optical path difference is adjusted, any one of the stage 33 and the piezo element 44 may be controlled, however, the optical path difference can be roughly adjusted by the control of the stage 33, and the optical path difference can be finely adjusted by the control of the piezo element 44.

Figure 6:
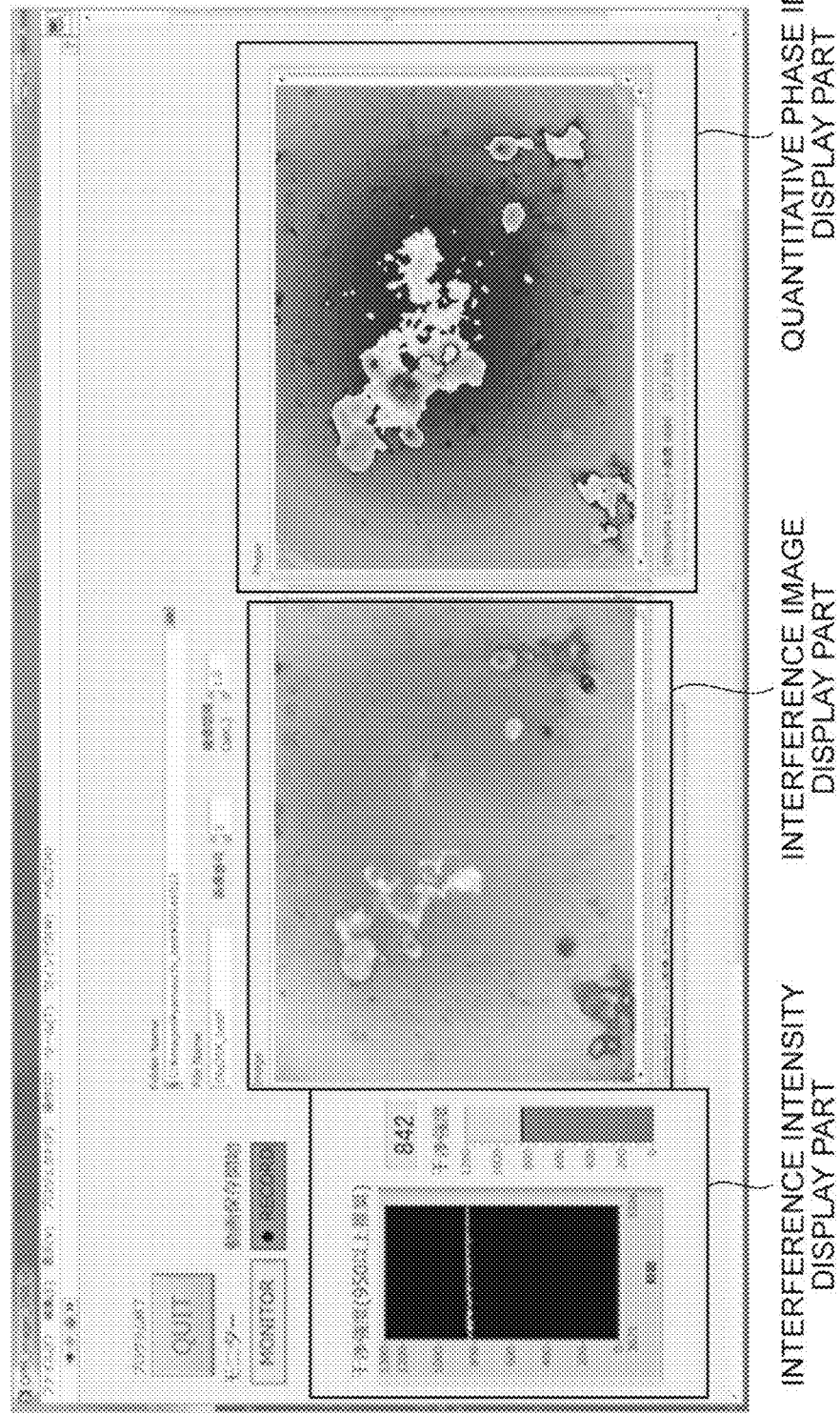
FIG. 6 is a diagram illustrating an example of information displayed on a display unit (display).

When the optical path difference is made small on the basis of the obtained interference intensity, the stage 33 may be automatically moved. Further, the interference intensity may be notified to the user to move the stage 33 by the user's operation. For example, the interference intensity is displayed on the display unit of the image acquisition unit 71 or the control unit 72, or a display unit separately provided from these units so as to notify the interference intensity to the user. The display unit may be a visual unit such as a display, an LED bar, an analog panel meter, or a digital panel meter, or an auditory unit such as a buzzer or a speaker which outputs a sound having a magnitude in accordance with the interference intensity, or further a tactile unit such as a vibrator which gives vibrations having a magnitude in accordance with the interference intensity to the user. The user moves the stage 33 in a direction of the optical axis of the objective lens 32 in order to increase the interference intensity which is displayed on the display unit. FIG. 6 is a diagram illustrating an example of information displayed on the display unit (display). In this example, the interference intensity is simultaneously displayed in three modes of a numerical value, a bar, and a graph showing temporal variation. Further, in this example, the interference image and a phase image (to be described below) are also displayed.

When the interference intensity is increased, it is most important that the optical path difference is minimized. However, even in a case where the focus or the optical axis of the imaging system of any one of the optical system on the sample side and the optical system on the reference side are deviated, the interference intensity is reduced. Therefore, the first thing to do for increasing the interference intensity is to adjust the optical path difference to be reduced, and further, to adjust the focus and the optical axis of each imaging system of the optical system on the sample side and the optical system on the reference side.

As an algorithm for maximizing the interference intensity, it is considered a method in which one of adjustment mechanisms (the optical path difference, the focus, and the optical axis) is moved in one direction while recording the interference intensity, the adjustment mechanism is moved in the reverse direction when the interference intensity passes by an optimal position and begins to be lowered, and a point at which the interference intensity is obtained within several % of error in maximum intensity obtained during scanning in one direction is considered as an optimal value. In a case where there are a plurality of adjustment points, an algorithm is considered in which the searching of such an optimal value is performed sequentially on each of the adjustment points, the adjustment is performed once more or in plural times as needed after one cycle of adjustment so as to realize an optimal state of the optical system as a whole.

Figure 17:
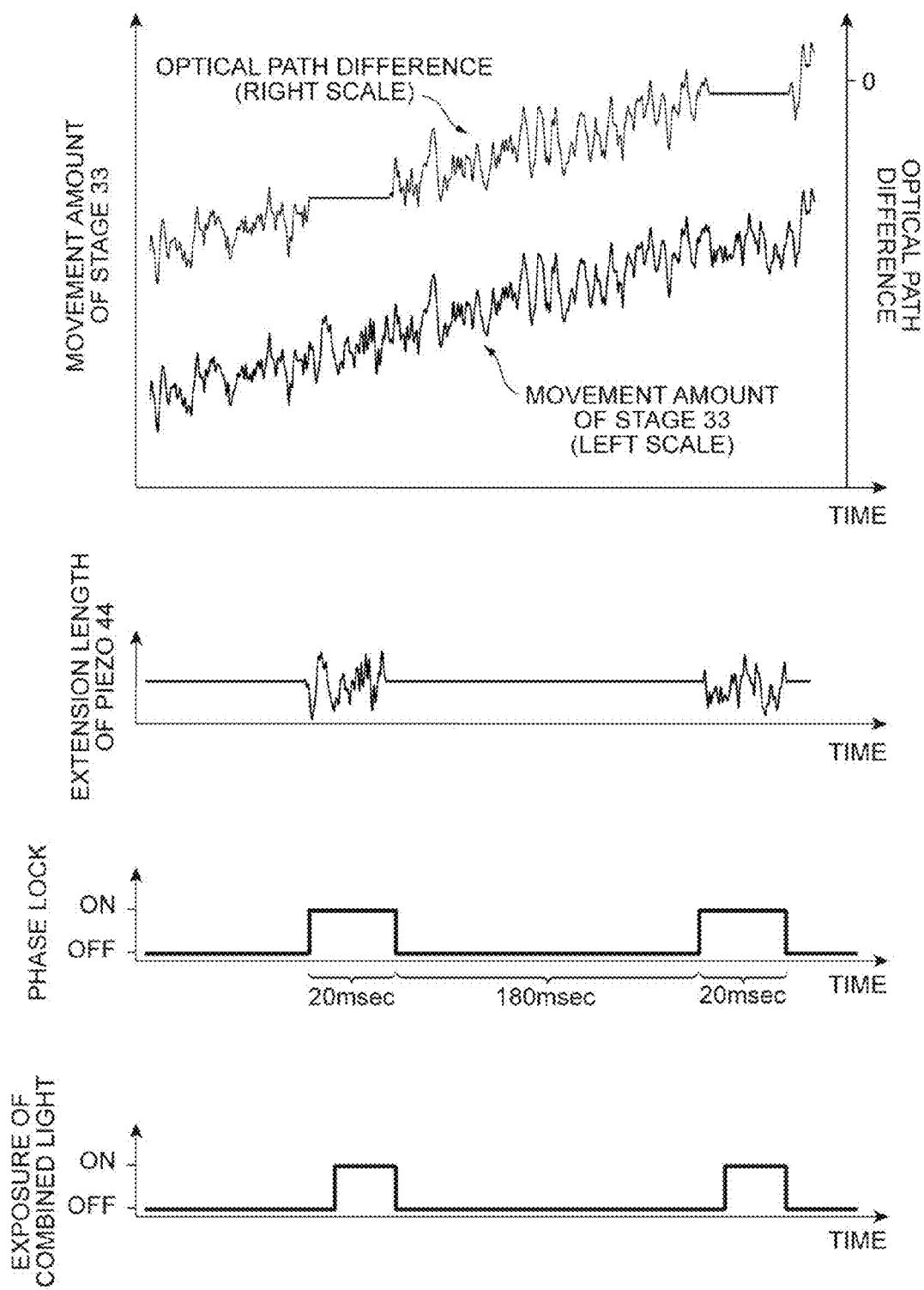
FIG. 17 is a diagram for describing a method of maximizing an interference intensity.

Further, as a method of maximizing the interference intensity, one or some of the adjustment mechanisms (the optical path difference, the focus, and the optical axis) may be moved while applying the phase lock intermittently. For example, in a case where the interference intensity is maximized while moving the stage 33 by the user's operation, an actual movement amount causes the vibration due to a mechanical factor of the optical system including the stage 33. Therefore, as illustrated in FIG. 17, when the interference optical system is adjusted while repeatedly turning ON and OFF the phase lock, the optical path difference is intermittently stabilized. FIG. 17 is a diagram for describing a method of maximizing the interference intensity. In this drawing, there are illustrated the temporal variations of the movement amount of the stage 33, the optical path difference, an extension length of the piezo element 44, turning ON/OFF of the phase lock, and turning ON/OFF of the imaging (exposure) of the combined light.

In a case where the interference optical system is adjusted while intermittently performing the phase lock as described above, the turning ON/OFF of the imaging (exposure) of the combined light by the imaging unit 61 may be performed in accordance with the turning ON/OFF of the phase lock. In this case, the imaging unit 61 is controlled such that an exposure period of the imaging unit 61 falls within the ON period of the phase lock. For example, the control unit 72 controls the imaging by the imaging unit 61 such that the exposure period of the imaging unit 61 falls within the ON period of the phase lock. For this reason, the user can confirm the interference image in which the phase lock is in the ON state periodically while adjusting the interference optical system, and therefore, the interference image can be confirmed without being affected with a mechanical factor.

In a case where the adjustment mechanism is moved while intermittently performing the phase lock and the interference image at timing when the phase lock is being applied is displayed, a target phase difference in each intermittent phase lock is preferably set to the same value at every cycle. In this case, the optical path difference L in the ON period of each phase lock is stabilized to $L = \Delta L + N\lambda$ (N is an integer, $\lambda$ is the center wavelength of the light source, and $\Delta L$ is an offset optical path difference corresponding to the phase difference). Therefore, a relative phase difference is constant at an imaging timing of each interference image even while the optical path difference is being adjusted. With this configuration, a pattern of the interference fringes is almost the same, and images only different in contrast can be sequentially acquired. Since information necessary for the purpose of maximizing the interference intensity is not the phase of the interference fringes but the contrast of the interference fringes, moving the adjustment mechanism while observing the interference image only different in contrast has less burden on an operator's work compared to moving the adjustment mechanism in a state where the interference fringes are changing.

In this way, the contrast of the interference fringes is useful as secondary information of the interference intensity. Further, shaking of the optical path difference additionally occurs even in the adjustment of the focus and the optical axis which are not directly related to the optical path difference. The method of moving the adjustment mechanism while intermittently performing the phase lock is effective even in the adjustment of the focus and the optical axis.

There is a need to appropriately set a ratio of the ON period of the phase lock and the OFF period of the phase lock and a cycle of repeating ON and OFF of the phase lock. First, when the ON period of the phase lock is too short, it is insufficient for stabilizing the phase lock, and an exposure time is short when the imaging unit 61 performs the exposure. Therefore, since the phase lock mechanism can be stabilized in the optical path length in a transition time (depending on a mechanical factor of the optical system) of about 1 msec to 5 msec, it is preferable that the ON period of the phase lock be longer than at least 1 msec. Here, in a case where a sample (for example, glass surface) having a low reflectance is observed, it is preferable to take a time width for enabling to capture an image of the interference fringes with a sufficient light amount, and it is preferable to set the time width to at least 20 msec or longer from the viewpoint of the exposure period of the imaging unit 61.

On the other hand, there may be a problem even when the ON period of the phase lock is too long. The cycle of repeating ON and OFF of the phase lock cannot be set to be smaller than the reciprocal of the ON period of the phase lock. For example, when the ON period of the phase lock is 5 seconds, it is a matter of course that the cycle repeating ON and OFF of the phase lock also has to be longer than 5 seconds. In this case, since the cycle of displaying the interference image becomes longer than 5 seconds, operability of the operator is degraded. Further, in a case where the ON period of the phase lock is long, there also occurs a problem related to the extension range of the piezo element 44. An extension distance of the piezo element 44 is adjusted by the feedback control in order to remove a change in the optical path length caused by the movement of the adjustment mechanism (the optical path difference, the focus, and the optical axis) during the phase lock is turned ON, however, the extension range of the piezo element 44 to be used in the feedback control is about ±8 μm at most, and in a case where the change in the optical path length caused by the movement of the adjustment mechanism (the optical path difference, the focus, and the optical axis) exceeds the range, the feedback control does not work. For these reasons, the ON period of the phase lock is preferably 3 seconds or less for example.

Further, since the cycle of repeating ON and OFF of the phase lock becomes the same as the cycle of displaying the interference image, for operability of the operator being not degraded, the cycle is preferably set to be less than 3 seconds. In a case where the ON period of the phase lock and the cycle of repeating ON and OFF of the phase lock are preferably set, the time width of the OFF period of the phase lock is also obtained automatically.

FIG. 17 illustrates a timing chart in a case where the optical path length is adjusted while the phase lock is intermittently performed, and also illustrates specific numerical values of the length of each period. The ON period of the phase lock is set to 20 msec, and the cycle of repeating ON and OFF of the phase lock is set to 200 msec. In this modification, the interference image can be stably obtained with the interval of 200 msec.

Further, the OFF period of the phase lock may be set to 30 msec or less. Since the interference image is not acquired in the OFF period of the phase lock, the interference image is not smoothly changed for the operator when the OFF period of the phase lock is larger than 30 msec, and therefore, the observation is not easy. For this reason, the OFF period of the phase lock is set to 30 msec or less to enable smooth change of the interference image for the operator. Further, the OFF period and the ON period of the phase lock are set, and the cycle of repeating ON and OFF of the phase lock may be calculated, and the OFF period of the phase lock and the cycle of repeating ON and OFF of the phase lock are set, and the ON period of the phase lock may be set.

Figure 18:
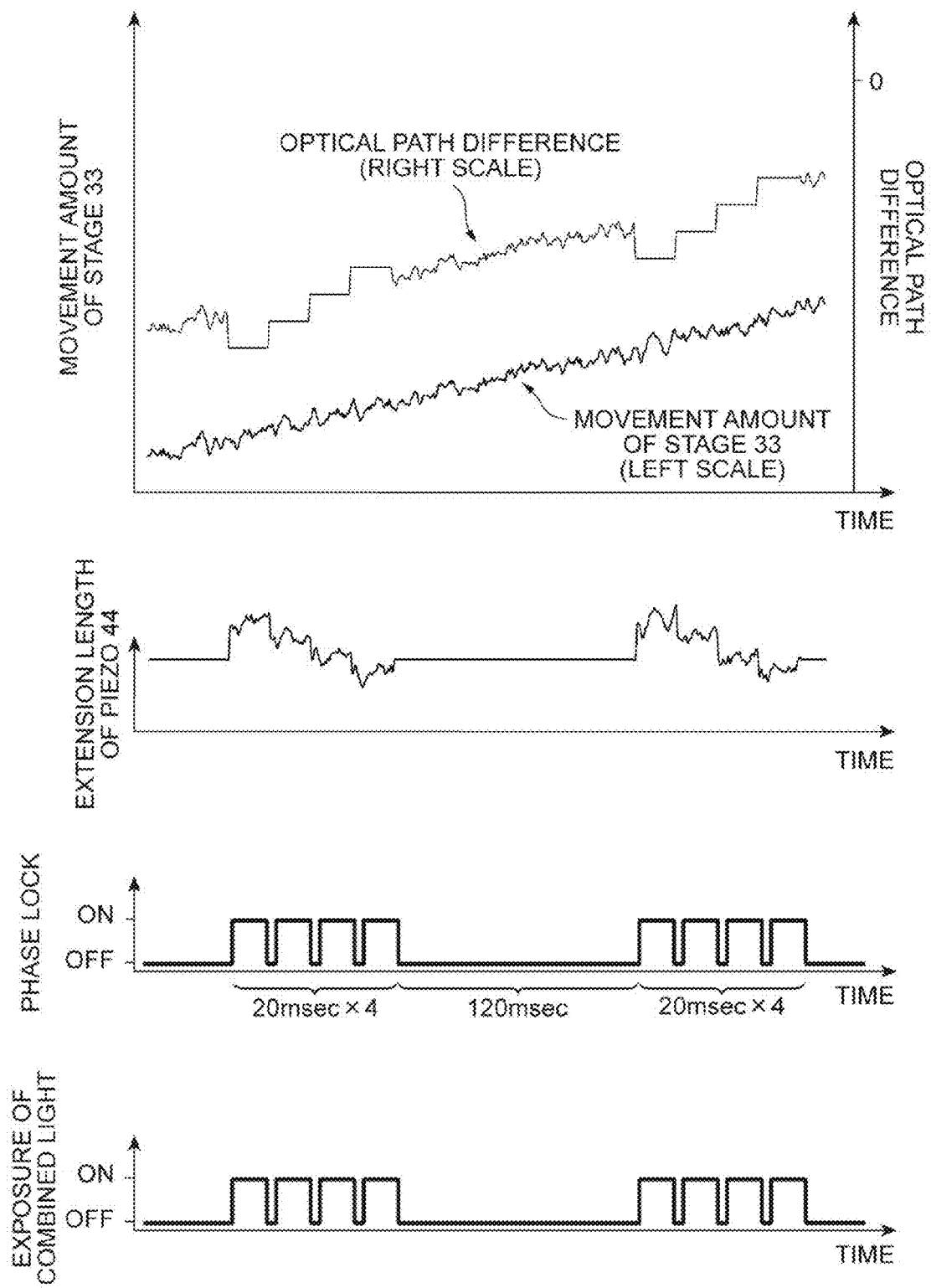
FIG. 18 is a diagram for describing another method of maximizing the interference intensity.

Further, as illustrated in FIG. 18, the phase shift may be performed with the intermittent phase lock. FIG. 18 is a diagram for describing another method of maximizing the interference intensity. The drawing also illustrates the temporal variations of the movement amount of the stage 33, the optical path difference, the extension length of the piezo element 44, turning ON/OFF of the phase lock, and turning ON/OFF of the exposure of the combined light. In the timing chart illustrated in the drawing, the phase shift is performed during a period of each phase lock. Specifically, a plurality (4 times in FIG. 18) of ON periods of the phase lock are intermittently provided while interposing stagnation periods, and the phase shift is performed during a period of each phase lock. Thereafter, the OFF period of the phase lock is provided, a plurality of periods of the phase lock are intermittently provided again while interposing the stagnation periods, and the phase shift is performed during a period of each phase lock again. As a phase shift method, it is preferable to use a weft-known λ/4 phase shift method. In the method illustrated in FIG. 18, the optical path difference is adjusted while the phase lock is intermittently performed, so that the interference image and the phase image are obtained at an interval of 200 msec even while adjusting the optical path difference.

Next, an example of the interference observation apparatus 1 will be described. The configuration illustrated in FIG. 1 is used. An LED having a wavelength of 610 nm is used as the light source 10. A camera equipped with the CCD area image sensor is used as the imaging unit 61. Further, a photodiode is used as the photodetector 62.

As the observation object, a HeLa cell from a cervical cancer is cultured on a holding substrate formed of a half mirror, and fixed with ethanol. At the time of observation, several drops of the pure water are trickled onto the cell, a cover glass is set thereon, and the cell is observed by the objective lens 32 from the upper side.

The angular frequency ca of the vibration of the reference mirror 41 caused by the piezo element 44 is set to 2.3 kHz. The components of 2.3 kHz and 4.6 kHz in the detection signal output from the photodetector 62 are synchronously detected by the control unit 72. The phase difference Δϕ is obtained from the above Formula (5) on the basis of the synchronous detection result, and the center position of the vibration of the reference mirror 41 caused by the piezo element 44 is subjected to the feedback control on the basis of the phase difference Δϕ to perform the phase lock and the phase shift.

Figure 7:
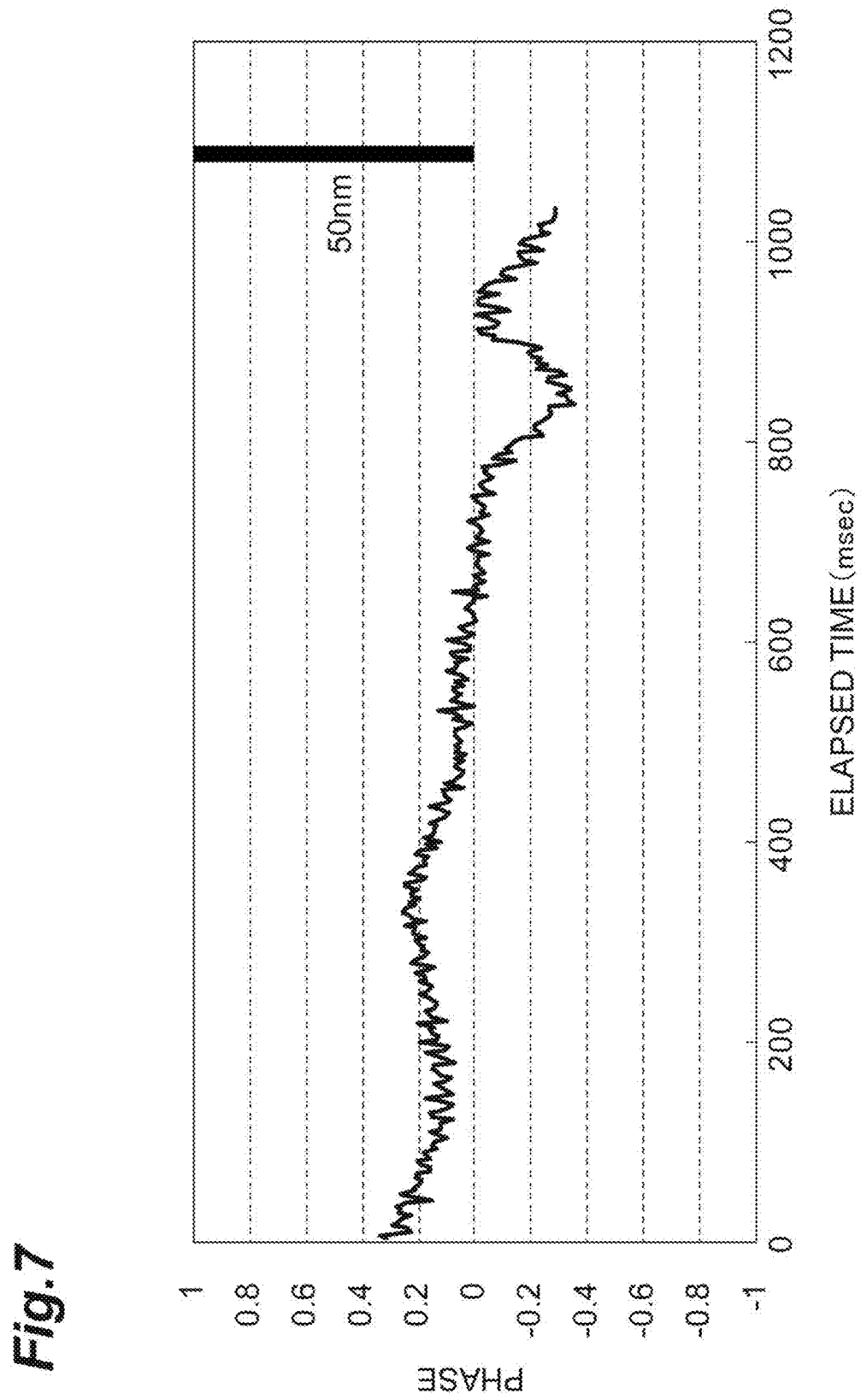
FIG. 7 is a graph illustrating a temporal variation in phase in a case where feedback control is not performed.
Figure 8:
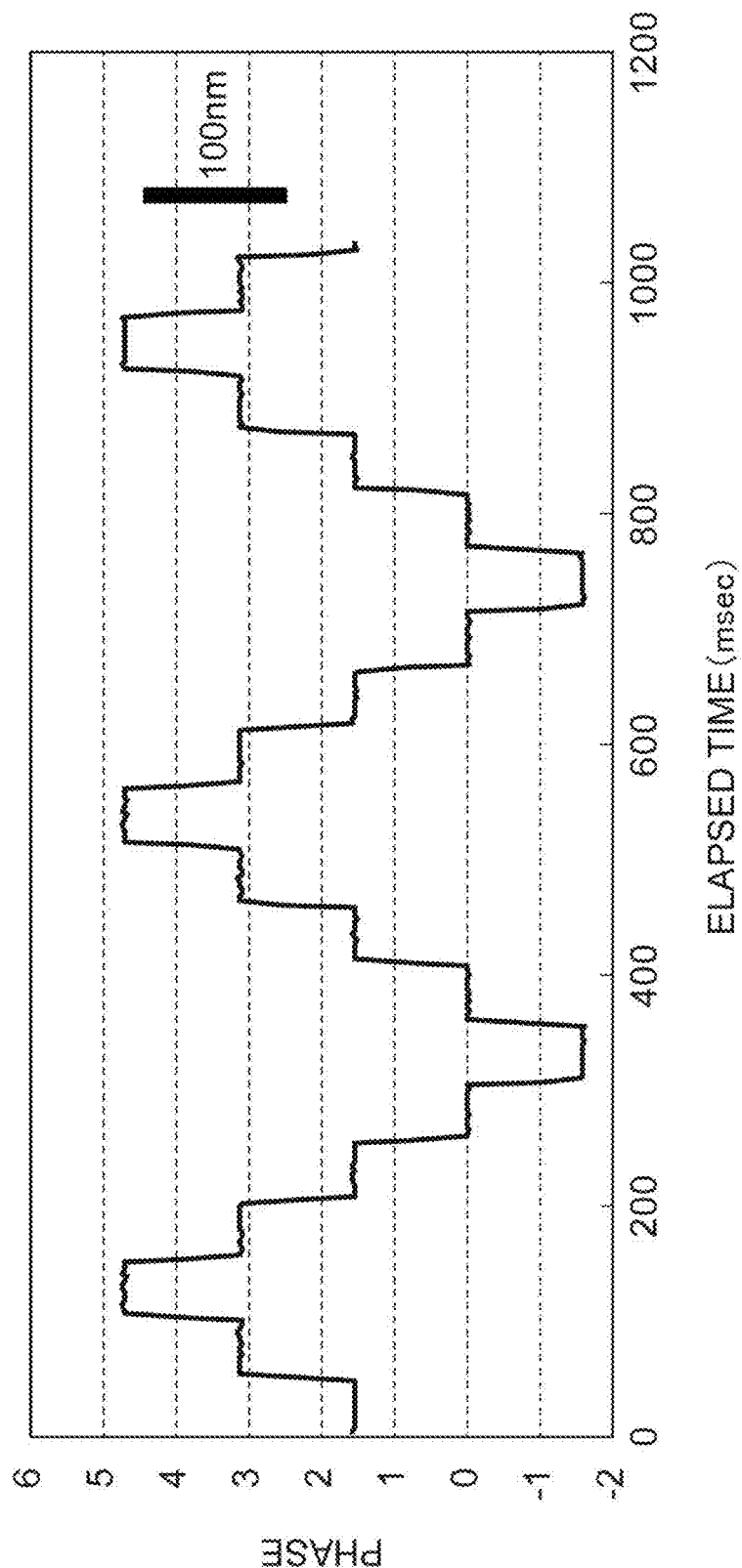
FIG. 8 is a graph illustrating a temporal variation in phase in a case where the feedback control is performed.

FIG. 7 is a graph illustrating a temporal variation of the phase in a case where the feedback control is not performed. FIG. 8 is a graph illustrating a temporal variation of the phase in a case where the feedback control is performed. In a case where the feedback control is not performed (FIG. 7), a drift of the optical path length of about 10 nm per second is recognized. On the other hand, in a case where the feedback control is performed (FIG. 8), the phase shift and the phase lock are exactly realized by π/2.

Figure 9:
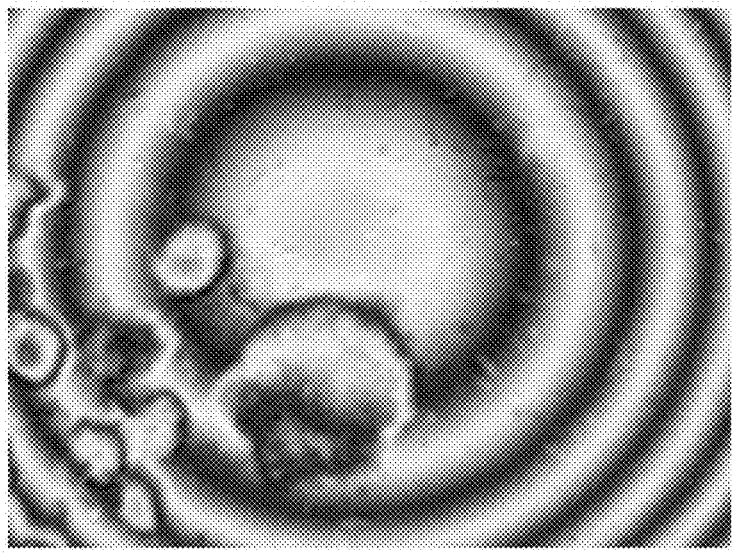
FIG. 9 includes views showing interference images.
Figure 9:
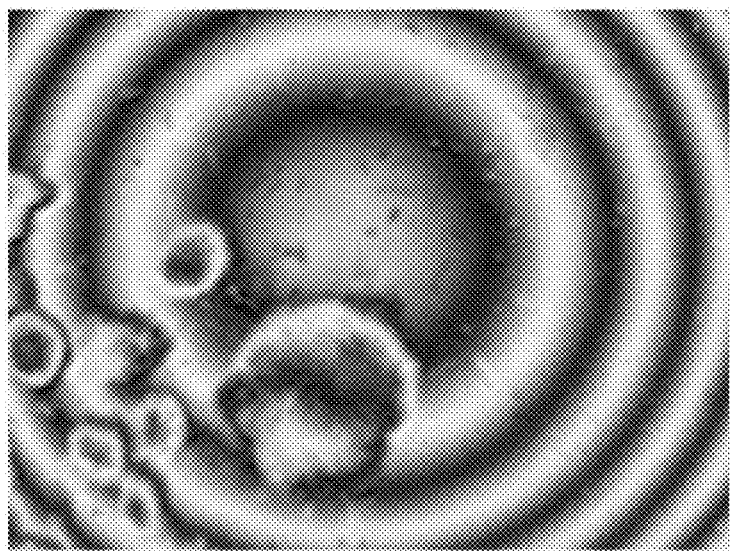
Figure 10:
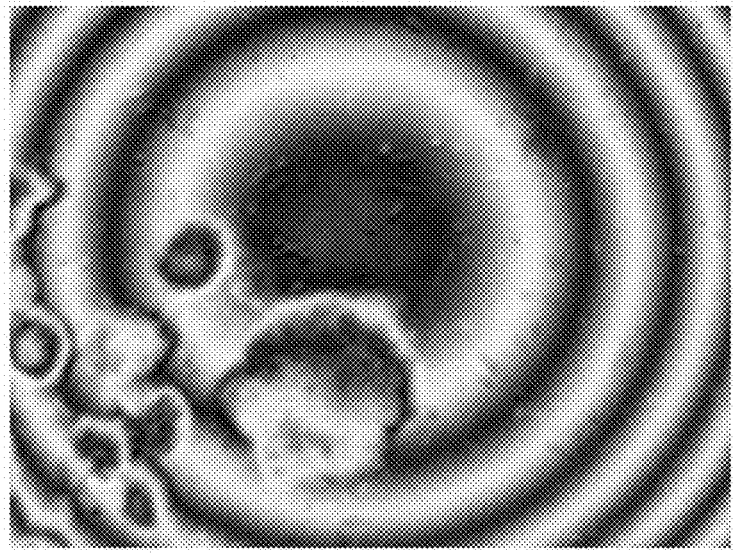
FIG. 10 includes views showing interference images.
Figure 10:
Figure 11:
FIG. 11 is a view showing a phase image.

FIG. 9 and FIG. 10 include views showing the interference images acquired by performing the phase shift and the phase lock. An interference image $I_2(x, y)$ shown in (b) in FIG. 9 is different from an interference image $I_1(x, y)$ shown in (a) in FIG. 9 in phase by π/2, an interference image $I_3(x, y)$ shown in (a) in FIG. 10 is different in phase by n, and an interference image $I_4(x, y)$ illustrated in (b) in FIG. 10 is different in phase by 3π/2. A quantitative phase image Ω(x, y) is obtained from these interference images $I_1$ to $I_4$ by the following Formula (11). Further, x and y are variables indicating the positions in the respective images. The image Ω(x, y) is subjected to phase unwrapping, and a distortion component of the background is flattened by the calculation of the shading correction using a Zernike polynomial, so that the quantitative phase image shown in FIG. 11 is obtained.

[Formula 11]

$$\psi(x, y) = \tan^{-1}\left(\frac{I_1(x, y) - I_3(x, y)}{I_4(x, y) - I_2(x, y)}\right) \quad (11)$$

Next, the effects of the present embodiment will be described. In the present embodiment, since there is provided one light source which outputs the incoherent light, the configuration can be made at a low cost compared to the configuration (configuration disclosed in Non Patent Document 5) in which two light sources of a laser light source and an inherent light source are included. Further, the configuration can be easily set up when the apparatus is assembled and readjusted after conveyance.

Further, since the interference image is acquired using the incoherent light in the present embodiment, speckles and diffraction noises are suppressed, so that the acquired interference image can have a good image quality. In the present embodiment, since the phase lock and the phase shift can be made with accuracy, a high-speed sweeping of the optical path difference and a high-speed imaging are not necessary, and the quantitatively excellent interference image can be acquired without irradiating the observation object with high intensity light.

Figure 19:
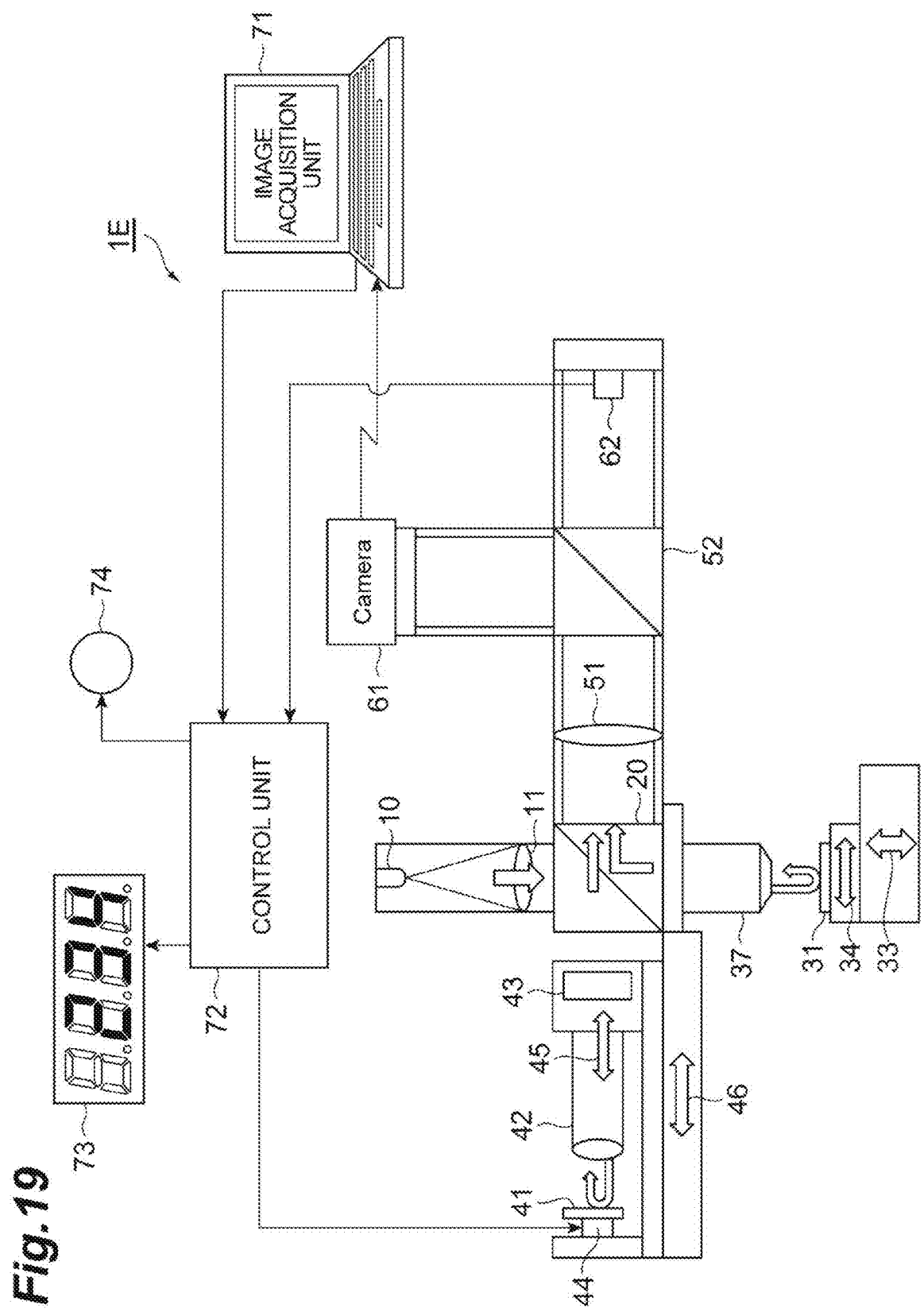
FIG. 19 is a diagram illustrating a configuration of an interference observation apparatus 1E.

Next, another modification of the interference observation apparatus 1 will be described using FIG. 19. FIG. 19 is a diagram illustrating a configuration of an interference observation apparatus 1E. The interference observation apparatus 1E illustrated in FIG. 19 is different from the configuration illustrated in FIG. 2 in that an objective lens 37 with a correction collar is provided in place of the objective lens 32, and different in that a numerical value display 73 and a speaker 74 are further provided. As a display for displaying the interference intensity, the numerical value display 73 and the speaker 74 are used. For example, the objective lens 37 of the magnification of 20 with the correction collar is used as the objective lens. An LED having a wavelength of 610 nm is used as the light source 10. A camera equipped with the CCD area image sensor is used as the imaging unit 61. Further, the photodiode is used as the photodetector 62.

This modification has a feature that the objective lens 37 with the correction collar is used. The objective lens with the correction collar includes a mechanism which moves the lens provided therein in a direction of the optical axis, and corrects aberration caused by a transparent object when observing the sample surface over the transparent object such as a slide glass, and a high-resolution image can be acquired.

Figure 20:
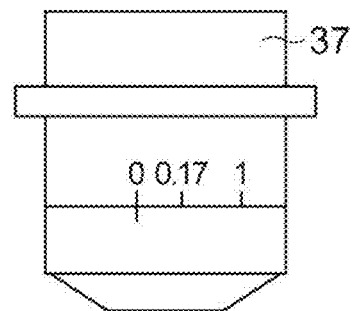
FIG. 20 includes diagrams for schematically describing a focus in a case where a sample 101 over a transparent object is observed using an objective lens 37 with a correction collar.
Figure 20:
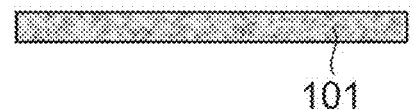
Figure 20:
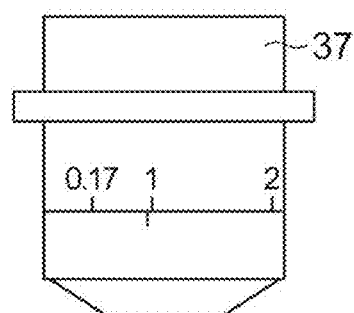
Figure 20:
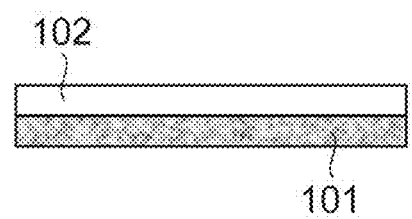

FIG. 20 includes diagrams for schematically describing a focus in a case where a sample 101 over a transparent object is observed using the objective lens 37 with the correction collar. As illustrated in (a) in FIG. 20, when a first surface of the sample 101 is observed without the transparent object, a value of the correction collar of the objective lens 37 is set to 0 mm, and the sample 101 is placed at a position of a designed focal length to obtain a focused image of the sample 101. On the other hand, when the surface of the sample 101 is observed over a transparent object 102 such as a slide glass as illustrated in (b) in FIG. 20, the sample 101 is moved in a direction of the optical axis after the value of the correction collar is appropriately set in accordance with a thickness of the transparent object 102, so that a focused image of the sample 101 can be obtained. Herein, a thing requiring attention is that not only the adjustment of the correction collar but also the position of the sample 101 in a direction of the optical axis is also necessarily adjusted depending on the presence/absence of the transparent object 102 in order to obtain the focused image of the sample 101.

As the observation object, a cell is observed from the upside by the objective lens 32 using a test chart for a microscope in which chromium is deposited with a thickness of about 100 nm on the glass. The observation is performed on two cases: a case where the slide glass is not placed on the test chart; and a case where the slide glass is placed.

The angular frequency w of the vibration of the reference mirror 41 caused by the piezo element 44 is set to 20 kHz. The components of 20 kHz and 40 kHz in the detection signal output from the photodetector 62 are synchronously detected by the control unit 72. The phase difference $\Delta\phi$ is obtained from the above Formula (5) on the basis of the synchronous detection result, and the center position of the vibration of the reference mirror 41 caused by the piezo element 44 is subjected to the feedback control on the basis of the phase difference $\Delta\phi$ to perform the phase lock and the phase shift. The cycle (=acquisition cycle of the interference image) of the phase shift is set to an interval of 67 msec, and the phase image is acquired at an interval of 268 msec using a four-point phase shift method with the interval of $\pi/2$.

As the interference intensity, the AC in Formula (6) is calculated by the control unit 72 and converted in a logarithmic scale. In practice, a value of $20 \times \log_{10}$ (AC) is calculated, and the calculation result is displayed on the numerical value display 73. Further, the speaker 74 is driven by a rectangular wave with a frequency positively correlating with the value of $20 \times \log_{10}$ (AC) to make a beep sound. With the configuration, a low-frequency beep sound is output when the AC value is low, and a high-frequency beep sound is output when the AC value is high. The display value of the interference intensity and the frequency of outputting the sound are updated by a cycle of 50 msec. Since the update interval of the display value of the interference intensity is faster than the acquisition cycle of the interference image and the phase image, the optical adjustment can be efficiently performed compared to referring the interference image.

Figure 21:
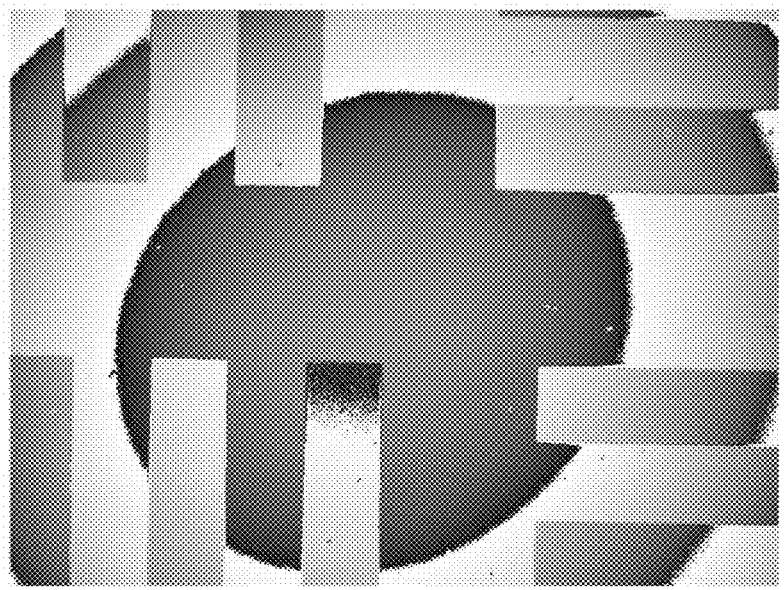
FIG. 21 includes views showing quantitative phase images before and after phase unwrapping.
Figure 21:
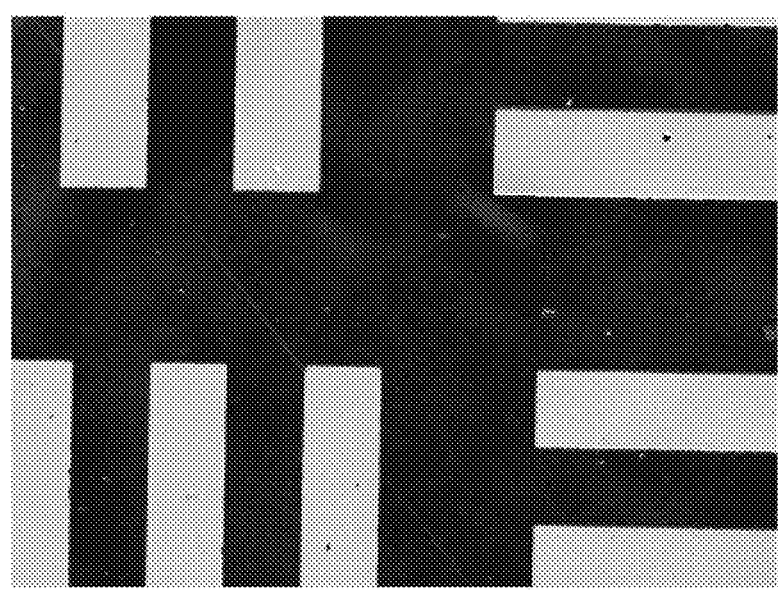

First, the interference image and the phase image are observed while nothing is placed on the test chart. The value of the correction collar of the objective lens is set to 0 mm. The display value of the numerical value display 73 and the beep sound from the speaker 74 are used as an index, and the stage 45 and the stage 46 are moved in a direction of the optical axis such that the interference intensity is maximized, and then the clear interference image and the quantitative phase image $\Omega(x, y)$ are obtained. The quantitative phase image (before phase unwrapping) is illustrated in (a) in FIG. 21. Further, x and y are variables indicating the positions in the respective images. When the image $\Omega(x, y)$ is subjected to the phase unwrapping, and the distortion component of the background is flattened by calculating the shading correction using the Zernike polynomial, the quantitative phase image illustrated in (b) in FIG. 21 is obtained. A focused image with high accuracy is obtained.

Next, the slide glass of a nominal thickness of 0.8 mm to 1.0 mm is placed on the test chart, and the interference image and the phase image are observed. The value of the correction collar of the objective lens is set to 0.9 mm Compared to the case of no slide glass, the focused image of the sample is obtained by moving down the sample stage by 390 μm. After focusing, the entire reference optical system is moved in a direction of the optical axis using the stage 46 to maximize the interference intensity with the display value of the numerical value display 73 and the beep sound from the speaker 74 as an index. The positive moving direction of the stage 46 is a direction where the optical path length of the reference optical path becomes long.

Figure 22:
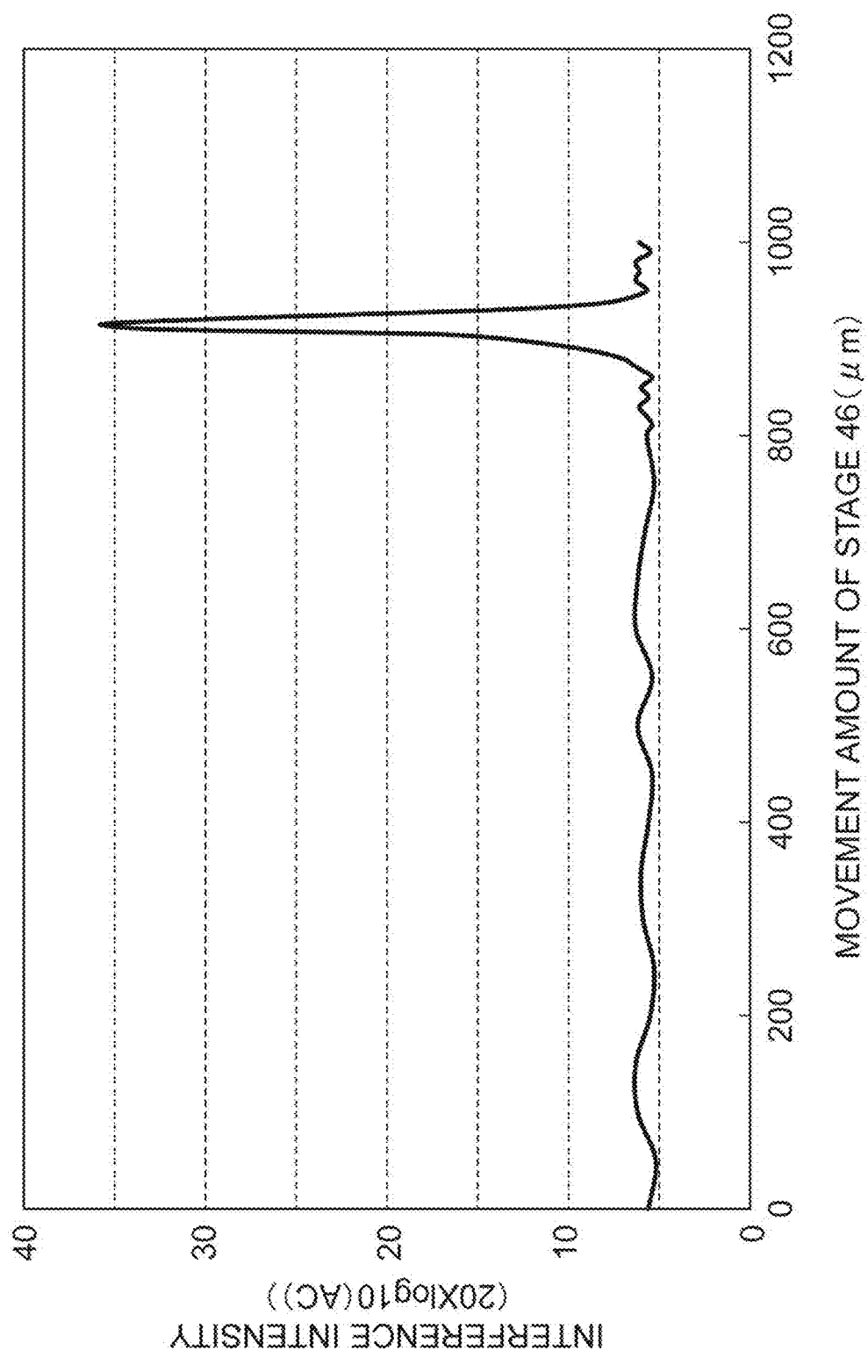
FIG. 22 is a graph illustrating a relation between a movement amount of a stage 46 and an interference intensity display value.

A relation between the movement amount of the stage 46 and an interference intensity display value is illustrated in FIG. 22. The interference intensity ($=20 \times \log_{10}$ (AC)) before the movement of the stage 46 is about 5.0, the interference intensity is maximized to 35.8 in the vicinity of an movement amount of 915 μm of the stage 46. Further, the frequency of the beep sound output from the speaker 74 is 520 Hz before the movement of the stage 46, and is 2600 Hz when the stage 46 is moved to maximize the interference intensity.

Considering that the thickness of the slide glass is about 900 μm, and the refractive index difference between the slide glass and the air is 0.5, an increment of the optical path length caused from the refractive index difference is considered as about 450 μm one way. Further, since the sample stage is moved to adjust a focus, an increment of 390 μm one way is generated in the optical path length. In addition, the inner lens is moved by the adjustment of the correction collar of the objective lens, and thus the optical path length is changed about 75 μm one way. With these multiple factors, it is considered that the optical path length on the sample side is increased by 915 μm compared to that before inserting the slide glass.

Figure 23:
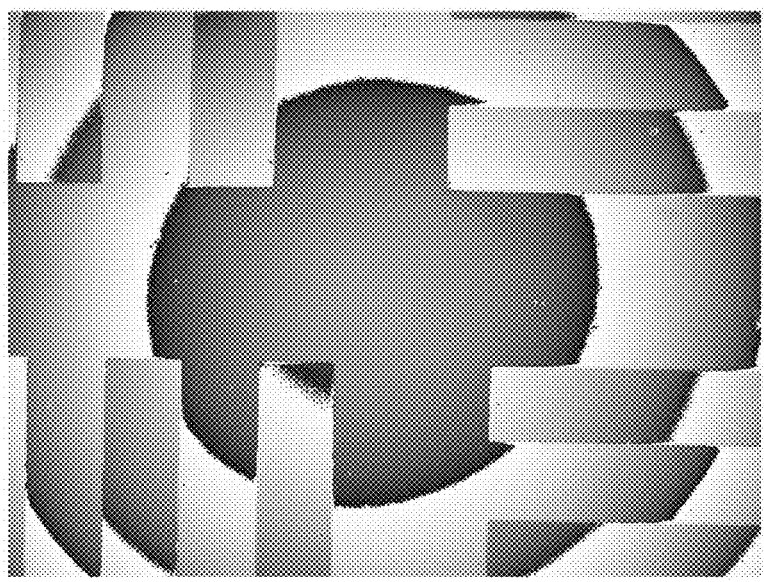
FIG. 23 includes views showing quantitative phase images before and after phase unwrapping.
Figure 23:

(a) in FIG. 23 illustrates the quantitative phase image (before phase unwrapping) obtained in a state where the slide glass is placed on the test chart. Further, x and y are variables indicating the positions in the respective images. When the image $\psi(x, y)$ is subjected to the phase unwrapping, and the distortion component of the background is flattened by calculating the shading correction using the Zernike polynomial, the quantitative phase image illustrated in (b) in FIG. 23 is obtained. Similarly to the case before the slide glass is inserted, a focused image with high accuracy is obtained.

Next, the description will be given about the effects of the present embodiment in a case where the objective lens with the correction collar is used. In a case where there is a transparent object such as the slide glass on the sample, a wavefront aberration of the observation light caused by the thickness of the transparent object is corrected using the objective lens with the correction collar, so that a focused image with high accuracy can be obtained. However, the sample light and the reference light necessarily have the same optical path length in an interference observation optical system using the incoherent light, and without the display unit such as the numerical value display 73 and the speaker 74 in the present embodiment, it is difficult to set the optical path lengths of the sample light and the reference light to be equal by the user's operation. Further, in a case where an apparatus is specialized to the sample having a specific thickness of the transparent object to fix the correction collar and the optical path length on the reference optical path side, the apparatus is not possible to be used for the sample having a different thickness of the transparent object; and versatility is degraded. In the present embodiment, the user adjusts the correction collar of the objective lens with the correction collar for the sample with the transparent object having an arbitrary thickness, and adjusts the optical path length on the reference optical path side with the display unit such as the numerical value display 73 and the speaker 74 as an index, and therefore, there is a merit in that the quantitative phase image with high accuracy can be obtained with versatility and high operability.

As the observation object sample of the present embodiment, a flat panel display having electric element below the glass surface or an electric element sealed below an optical film may be considered. Further, a semiconductor such as silicon is transparent for near infrared light having a wavelength of 1000 nm or more, and even in a case where the wiring surface of the semiconductor integrated circuit is observed over the silicon using the incoherent near infrared light is within a range of the present modified embodiment. Further, the present embodiment is not limited to a solid object with respect to the transparent object, and the present embodiment is effective even in a case where the sample such as a cell is observed over a transparent liquid such as a culture solution.

Second Embodiment

Figure 12:
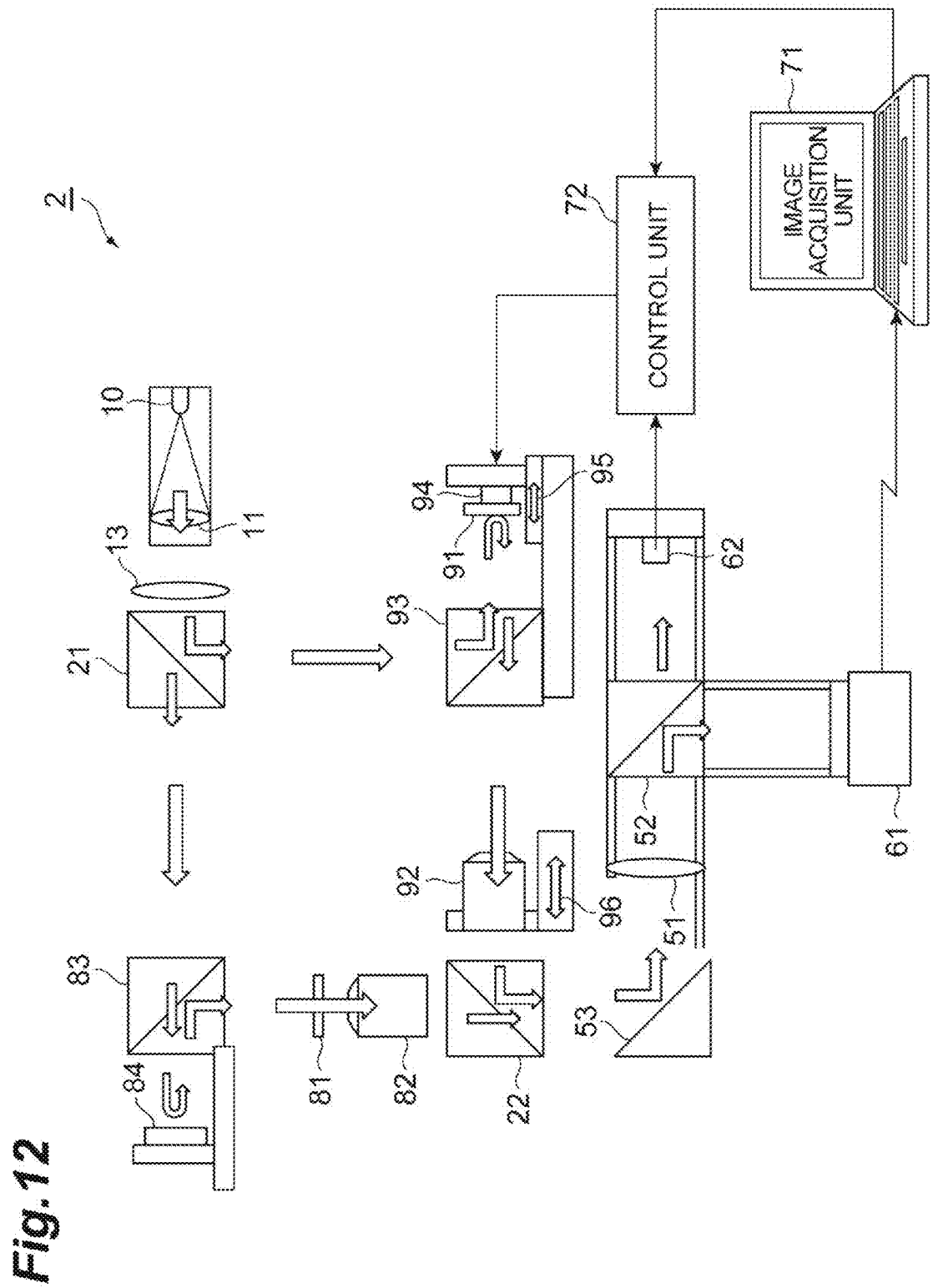
FIG. 12 is a diagram illustrating a configuration of an interference observation apparatus 2.

FIG. 12 is a diagram illustrating a configuration of an interference observation apparatus 2 of a second embodiment. The interference observation apparatus 2 includes a light source 10, a lens 11, a lens 13, a beam splitter 21, a beam splitter 22, a sample holding table 81, an objective lens 82, a beam splitter 83, a fixed mirror 84, a reference mirror 91, an objective lens 92, a beam splitter 93, a piezo element 94, stages 95 and 96, a tube lens 51, a beam splitter 52, a mirror 53, an imaging unit 61, a photodetector 62, an image acquisition unit 71, and a control unit 72.

The interference observation apparatus 2 includes an optical system of the Mach-Zehnder interferometer, and acquires an interference image on the basis of the light transmitted through an observation object held on the sample holding table 81. The observation object is not limited to a specific cell or biological sample. For example, the observation object includes a cultured cell, an immortalized cell, a primary cultured cell, a cancer cell, a fat cell, a liver cell, a cardiac muscle cell, a nerve cell, a glia cell, a somatic stem cell, an embryonic stem cell, a pluripotential stem cell, an iPS cell, and a cell aggregation (spheroid) created on the basis of at least one of these cells. Further, the observation object is not limited to a biological object, and includes an industrial sample which can be measured in the transmission type configuration, for example, an inner portion of glass, an inner portion of a semiconductor element, a resin material, a liquid crystal, a high molecular compound, and an optical element.

The light source 10 outputs incoherent light. The light source 10 may be, for example, a lamp light source such as a halogen lamp, an LED (Light emitting diode) light source, an SLD (Super luminescent diode) light source, or an ASE (Amplified spontaneous emission) light source, or the like. The lenses 11 and 13 condense the light output from the light source 10 to the observation object which is held on the sample holding table 81.

The beam splitter 21 and the beam splitter 22 form the Mach-Zehnder interferometer. The beam splitter 21 is optically coupled to the light source 10, inputs the light output from the light source 10 and passing through the lenses 11 and 13, and splits the light into two components to form first split light and second split light. The beam splitter 21 may be a half mirror for example. The beam splitter 21 outputs the first split light to the beam splitter 83 of the optical system on the measurement side, and outputs the second split light to the beam splitter 93 of the optical system on the reference side. The beam splitter 22 is optically coupled to the beam splitter 21, inputs the first split light which passes through the optical system on the measurement side, and inputs the second split light which passes through the optical system on the reference side, combines the thus input first split light and the second split light to output the combined light to the mirror 53. The beam splitter 22 may be a half mirror for example.

The optical system on the measurement side includes the sample holding table 81, the objective lens 82, the beam splitter 83, and the fixed mirror 84. The beam splitter 83 is optically coupled to the beam splitter 21 which forms the interference optical system, inputs the first split light output from the beam splitter 21 and outputs the light to the fixed mirror 84, and inputs the first split light reflected by the fixed mirror 84 and outputs the light to the sample holding table 81. The objective lens 82 inputs the first split light transmitting the observation object and outputs the light to the beam splitter 22. Further, a reflection mirror may be used in place of the beam splitter 83 and the fixed mirror 84.

The optical system on the reference side includes the reference mirror 91, the objective lens 92, the beam splitter 93, the piezo element 94, and the stages 95 and 96. The beam splitter 93 is optically coupled to the beam splitter 21 which forms the interference optical system, inputs the second split light output from the beam splitter 21 and outputs the light to the reference mirror 91, and inputs the second split light reflected by the reference mirror 91 and outputs the light to the objective lens 92. The objective lens 92 is optically coupled to the beam splitter 93, inputs the light arrived from the beam splitter 93, and outputs the light to the beam splitter 22. The piezo element 94 and the stage 95 move the reference mirror 91 in a direction of the optical axis of the optical system between the beam splitter 93 and the reference mirror 91. The stage 96 moves the objective lens 92 in a direction of the optical axis of the objective lens 92.

The tube lens 51 is optically coupled to the beam splitter 22 which forms the interference optical system, and forms an image on the imaging plane of the imaging unit 61 through the beam splitter 52 by the combined light output from the beam splitter 22 and reflected by the mirror 53. The beam splitter 52 is a splitting unit which is optically coupled to the beam splitter 22 forming the interference optical system and splits the light arrived from the lens 51, outputs one split light (first detection light) to the imaging unit 61, and outputs the other split light (second detection light) to the photodetector 62.

The light receiving unit which receives the combined light and outputs the detection signal includes the imaging unit 61 and the photodetector 62. The imaging unit 61 receives the first detection light arrived from the beam splitter 52 and outputs the received light signal (first detection signal). The imaging unit 61 is, for example, an image sensor such as a CCD area image sensor or a CMOS area image sensor. The photodetector 62 receives the second detection light arrived from the beam splitter 52 and outputs the received light signal (second detection signal). The photodetector 62 is, for example, a photodiode, an avalanche photodiode, a photomultiplier tube, a line sensor (linear sensor), a CCD area image sensor, or a CMOS area image sensor. The image acquisition unit 71 acquires the interference image on the basis of the first detection signal output from the imaging unit 61. The control unit 72 performs control on the basis of the second detection signal output from the photodetector 62.

Here, each of the image acquisition unit 71 and the control unit 72 is a computer which includes a processor and a memory. Further, the image acquisition unit 71 and the control unit 72 may be configured by individual computers, or may be configured by one computer. The computer may be, for example, a personal computer or a smart device such as a tablet terminal. Further, the image acquisition unit 71 or the control unit 72 may include an input unit (keyboard, mouse, tablet terminal, etc.) which receives an input from a user, and a display unit (display, tablet terminal, speaker, vibrator) which displays an interference intensity, etc. Further, in a case where the display unit can display a screen such as the display or the tablet terminal, the interference image etc. may be displayed with the interference intensity.

The light output from the light source 10 is formed as an image on the observation object in the optical system on the measurement side by the lenses 11 and 13, and further formed as an image on the respective light receiving planes of the imaging unit 61 and the photodetector 62 by the objective lens 82 and the tube lens 51. Further, the light output from the light source 10 is formed as an image at a specific position in the reference optical system by the lenses 11 and 13, and further formed as an image on the respective light receiving planes of the imaging unit 61 and the photodetector 62 by the objective lens 92 and the tube lens 51.

The piezo element 94 can finely adjust the optical path length in the optical system on the reference side (the optical system of the second split light). In place of the piezo element 44, an actuator such as a stepping motor or a servo motor may be used. The stage 95 can roughly adjust the optical path length in the optical system on the reference side. The piezo elements 94 and the stage 95 can adjust a difference between the optical path length of the optical system on the sample side (the optical system of the first split light) and the optical path length of the optical system on the sample side (the optical system of the first split light), and operates as an optical path difference adjusting unit which adjusts the optical path difference between the first split light and the second split light from the splitting to the combining in the interference optical system. The control unit 72 controls the optical path difference adjusting operation by the optical path difference adjusting unit (the stage 95, the piezo element 94).

The incoherent light output from the light source 10 is split into two components to form the first split light and the second split light by the beam splitter 21 through the lenses 11 and 13. The first split light is input to the fixed mirror 84 through the beam splitter 83 and reflected thereon. The reflected first split light is condensed to the observation object held on the sample holding table 31 through the beam splitter 83, and transmits the observation object. The transmitted first split light is input to the beam splitter 22 through the objective lens 82. The first split light has an optical delay when transmitting the observation object. The second split light is input to the reference mirror 91 through the beam splitter 93 and reflected thereon. The reflected second split light is input to the beam splitter 22 through the beam splitter 93 and the objective lens 92.

The first split light input from the objective lens 82 to the beam splitter 22, and the second split light input from the objective lens 92 to the beam splitter 22 are combined by the beam splitter 22. The combined light is split into two components by the beam splitter 52 through the mirror 53 and the tube lens 51, and received by the imaging unit 61, and received by the photodetector 62. The image acquisition unit 71 acquires the interference image on the basis of the first detection signal output from the imaging unit 61 which receives the combined light. Further, the control unit 72 controls the optical path difference adjusting operation by the optical path difference adjusting unit (the stage 95, the piezo element 94) on the basis of the second detection signal output from the photodetector 62 which receives the combined light.

Figure 13:
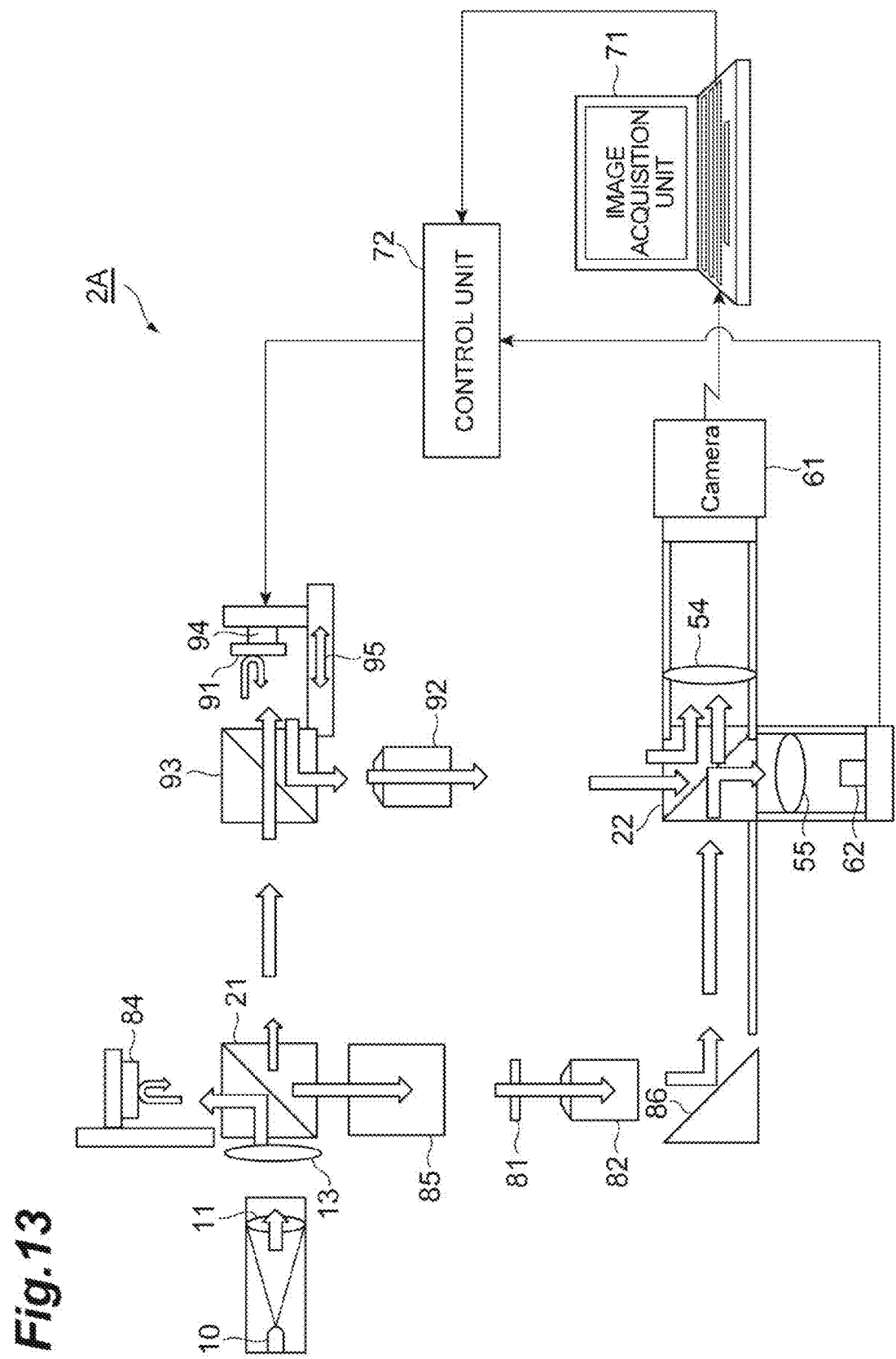
FIG. 13 is a diagram illustrating a configuration of an interference observation apparatus 2A.

FIG. 13 is a diagram illustrating a configuration of an interference observation apparatus 2A of a modification. The interference observation apparatus 2A is different from the configuration illustrated in FIG. 12 in that the beam splitter 21 also has a function of the beam splitter 83 in FIG. 12, the beam splitter 22 also has a function of the beam splitter 52 in FIG. 12, an optical path difference compensating plate 85 and a mirror 86 are provided, and the lens 54 and the lens 55 are provided in place of the lens 51. In the configuration illustrated in FIG. 13, the number of beam splitters is fewer by two compared to the configuration illustrated in FIG. 12, and thus it is possible to make cost down.

In order to acquire the interference image, the respective optical path lengths of the optical system on the measurement side (the optical system of the first split light) and the optical system on the reference side (the optical system of the second split light) have to be matched to each other. The observation object is a cell in a culture solution for example, and the culture solution may have a different component according to the object cell, and when the component is different, the refractive index is also different. Further, the thickness of a sample chamber for storing the observation object is also not limited to be fixed due to an influence of a manufacturing error and the like. Therefore, there is a need to confirm the optical path difference by sweeping the optical path difference to be applied to the optical system on the reference side at every time for various observation objects. For this reason, conventionally, it has been desirable that the laser light source is used in the transmission type interference observation apparatus.

On the other hand, the incoherent light source is used in the present embodiment. Further, the interference observation apparatus 2 may use a light source (halogen lamp, LED, or the like) which outputs spatially incoherent diffused light among the incoherent light sources. That is, in the interference observation apparatus 2, all the optical elements from the light source 10 to the objective lenses 82 and 92 have sufficiently large apertures (for example, 10 mm or more) compared to the beam diameter at the time when the light source 10 outputs the light, and therefore, incoherent illumination (that is, high NA illumination) can be spatially made using the incoherent light. The output light of the light source 10 can be condensed in the vicinity of the front focal planes of the objective lenses 82 and 92 by the two lenses 11 and 13 provided between the light source 10 and the beam splitter 21, so that the output light of the light source 10 can be used with high efficiency, and the high NA illumination can be realized.

Even in the second embodiment, the interference image is acquired using the incoherent light output by the light source 10, so that there is a need to control the optical path difference to perform the phase lock and the phase shift. Also in the second embodiment, using the first phase lock technique or the second phase lock technique described above, the control unit 72 obtains the phase difference in accordance with the optical path difference and also obtains the interference intensity, controls the optical path difference adjusting operation by the optical path difference adjusting unit (the stage 95, the piezo element 94), so that the optical path difference is made small on the basis of the obtained interference intensity and the optical path difference is kept constant on the basis of the obtained phase difference. Further, when the optical path difference is adjusted, any one of the stage 95 and the piezo element 94 may be controlled, however, the optical path difference can be roughly adjusted by the control of the stage 95, and the optical path difference can be finely adjusted by the control of the piezo element 94.

Next, an example of the interference observation apparatus 2A will be described. The configuration illustrated in FIG. 13 is used. An LED having a wavelength of 580 nm is used as the light source 10. The lens 13 is configured to condense the light approximately on the upper focal planes of the objective lenses 82 and 92. Since light transmits through a glass by additional one beam splitter in the optical system on the reference side, a glass plate having the same size as that of the beam splitter is inserted as the optical path difference compensating plate 85 in the optical system on the object side. The objective lenses of the magnification of 20 are used as the objective lenses 82 and 92.

A camera equipped with the CCD area image sensor is used as the imaging unit 61. Further, a photodiode is used as the photodetector 62. All the optical elements from the beam splitter 21 to the objective lenses 82 and 92 are configured to have apertures to sufficiently cover the beam diameter of the LED light at the positions.

A dried and fixed confluent HeLa cell is used as the observation object. At the time of observation, several drops of pure water are trickled onto the cell, a cover glass is set thereon, and the cell is observed by the Objective lens 82 from the lower side.

Figure 14:
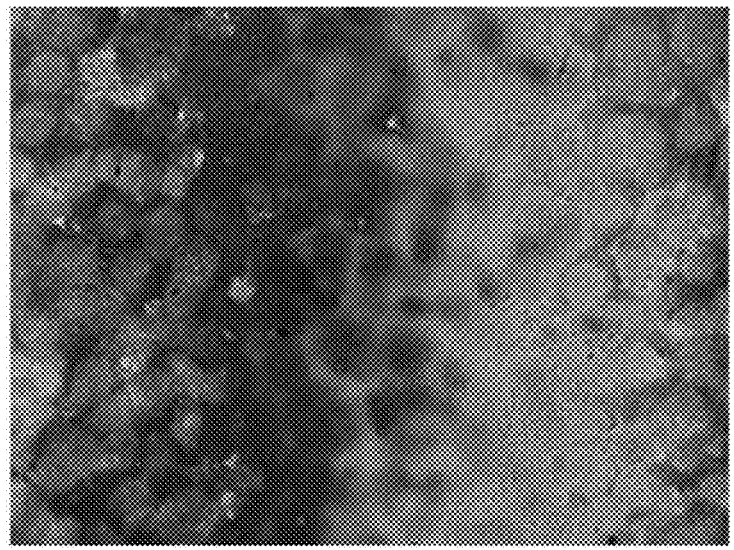
FIG. 14 includes views showing interference images.
Figure 14:
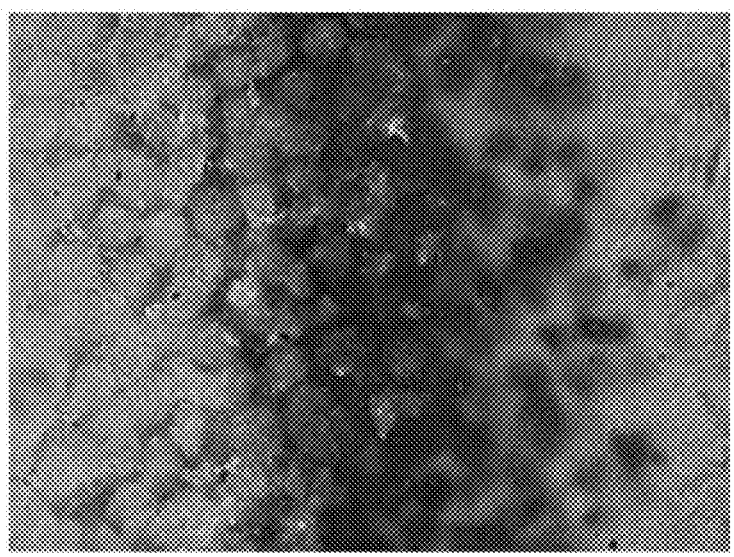
Figure 15:
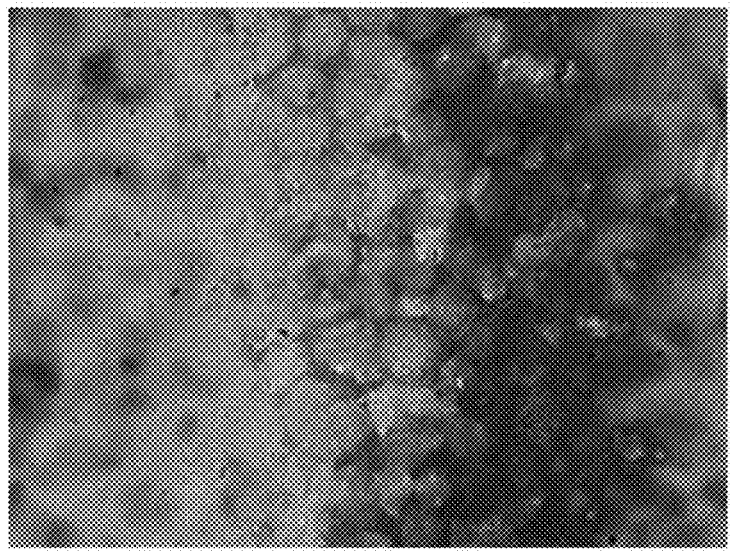
FIG. 15 includes views showing interference images.
Figure 15:
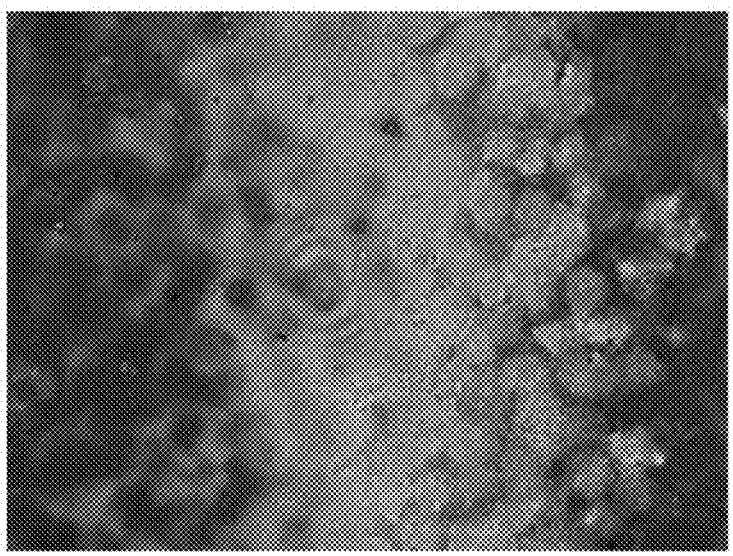
Figure 16:
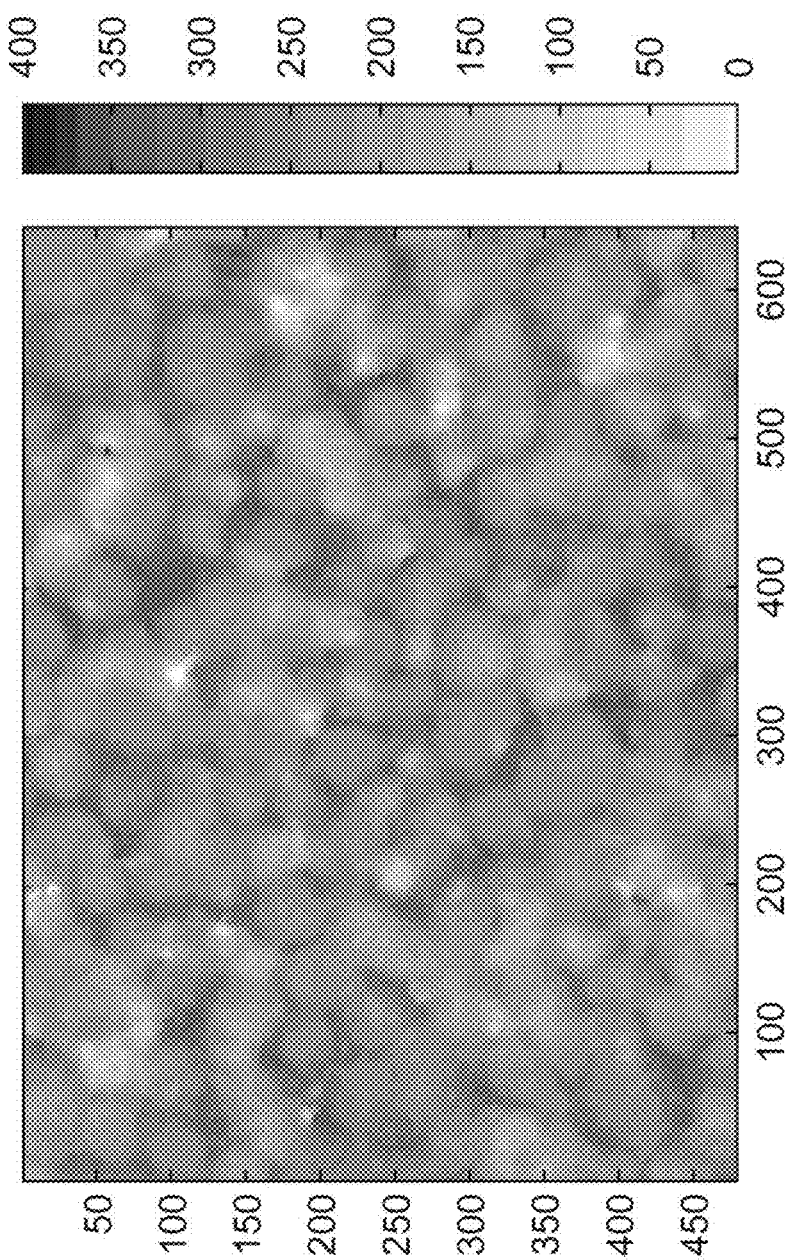
FIG. 16 is a view showing a phase image.

FIG. 14 and FIG. 15 include views showing the interference images acquired by performing the phase shift and the phase lock. An interference image $I_2(x, y)$ shown in (b) in FIG. 14 is different from an interference image $I_1(x, y)$ shown in (a) in FIG. 14 in phase by $\pi/2$, an interference image $I_3(x, y)$ shown in (a) in FIG. 15 is different in phase by $\pi$, and an interference image $I_4(x, y)$ shown in (b) in FIG. 15 is different in phase by $3\pi/2$. A quantitative phase image $\Omega(x, y)$ is obtained from these interference images $I_1$ to $I_4$ by the above Formula (11). The image $\Omega(x, y)$ is subjected to phase unwrapping, and a distortion component of the background is flattened by the calculation of the shading correction using a Zernike polynomial, so that the quantitative phase image shown in FIG. 16 is obtained.

Next, the effects of the present embodiment will be described. Even in the present embodiment, since there is provided one light source which outputs the incoherent light, the configuration can be made at a low cost compared to the configuration (configuration disclosed in Non Patent Document 5) in which two light sources of a laser light source and an inherent light source are included. Further, the configuration can be easily set up when the apparatus is assembled and readjusted after conveyance.

Further, since the interference image is acquired using the incoherent light even in the present embodiment, speckles and diffraction noises are suppressed, so that the acquired interference image can have a good image quality. Even in the present embodiment, since the phase lock and the phase shift can be made with accuracy, a high-speed sweeping of the optical path difference and a high-speed imaging are not necessary, and the quantitatively excellent interference image can be acquired without irradiating the observation object with high intensity light.

Further, in the present embodiment, there is used the light source 10 which outputs the spatially incoherent light so that the numerical aperture of the illumination for the observation object can be increased, and therefore, a spatial resolution is improved, and the diffraction noises and speckle noises are suppressed.

Further, in the present embodiment, the control unit 72 extracts an amplitude component of the detection signal (second detection signal) output from the photodetector 62, and obtains the interference intensity AC on the basis of the amplitude component of the detection signal, and therefore, the optical path difference can be easily adjusted to increase the interference intensity AC.

Modifications

The interference optical apparatus and the interference observation method according to one aspect of the present invention are not limited to the above-described embodiments and the configuration examples, and various modifications can be made.

The interference observation apparatus according to one embodiment of the present invention is an apparatus for acquiring an interference image of an observation object, and includes (1) a light source for outputting incoherent light, (2) an interference optical system for splitting the light output from the light source into first split light and second split light, reflecting or transmitting the first split light by an observation object, and combining the first split light and the second split light to output combined light, (3) a light receiving unit for receiving the combined light and outputting a detection signal, (4) an image acquisition unit for acquiring an interference image on the basis of the detection signal, and (5) the control unit for obtaining an interference intensity of the combined light on the basis of the detection signal, and adjusting the interference optical system to increase the interference intensity.

The interference observation method according to one embodiment of the present invention is a method for acquiring an interference image of an observation object, and includes (1) splitting incoherent light output from a light source by an interference optical system into first split light and second split light, reflecting or transmitting the first split light by an observation object, and combining the first split light and the second split light to output combined light, (2) receiving the combined light by a light receiving unit and outputting a detection signal, (3) acquiring an interference image on the basis of the detection signal by an image acquisition unit, and (4) obtaining an interference intensity of the combined light on the basis of the detection signal, and adjusting the interference optical system to increase the interference intensity.

Further, in the above interference observation apparatus or the interference observation method, it is preferable that a phase difference in accordance with an optical path difference between the first split light and the second split light from the splitting to the combining in the interference optical system is obtained on the basis of the detection signal, and the optical path difference in the interference optical system is kept constant on the basis of the phase difference.

Further, in the above interference observation apparatus or the interference observation method, it is preferable that the optical path difference in the interference optical system is adjusted to increase the interference intensity, and it is also preferable that an optical axis of an optical element on any one or both of optical paths of the first split light and the second split light in the interference optical system is adjusted to increase the interference intensity.

Further, in the above interference observation apparatus or the interference observation method, it is preferable that the interference intensity is displayed by a display unit. At this time, it is preferable that, by the display unit, a temporal variation of the interference intensity is displayed as a graph, or the interference intensity is displayed as a numerical value, or the interference intensity is output as a sound.

Further, in the above interference observation apparatus or the interference observation method, the interference optical system may include a Michelson interferometer, or the interference optical system may include a Mach-Zehnder interferometer.

Further, in the above interference observation apparatus or the interference observation method, the light receiving unit may include an image sensor for receiving the combined light and outputting a first detection signal, and a photodetector for receiving the combined light and outputting a second detection signal, the image acquisition unit may acquire the interference image on the basis of the first detection signal, and the control unit may obtain the phase difference and the interference intensity on the basis of the second detection signal.

Even any one of the first phase lock technique and the second phase lock technique may use a camera including a plurality of pixels arranged two-dimensionally as the photodetector 62 for the phase lock, so that the phase lock may be performed on the basis of the detection signal output from any one of the pixels.

Further, the phase lock may be performed on the basis of the detection signal output from any one of the pixels of the imaging unit 61. Further, there may be used one light receiving element which includes both of functions of the imaging unit 61 for acquiring the interference image and the photodetector 62 for the phase lock. In these cases, since the light receiving unit can be configured by one light receiving element, the apparatus can be made small, and the optical system can be easily adjusted.

Further, the interference intensity of the combined light may be Obtained on the basis of the detection signal output from the imaging unit 61 for acquiring the interference image. Further, the interference intensity of the combined light may be obtained on the basis of the detection signals respectively output from the imaging unit 61 and the photodetector 62.

In a state where a plurality of interference fringes appear in an image captured by the imaging unit 61, any of pixels arranged two-dimensionally in the imaging unit 61 is considered as an alternative of the line sensor or the plurality of photodetectors arranged one-dimensionally, and the interference intensity may be obtained by the second phase lock technique. Alternatively, similarly to the first phase lock technique, the piezo element is modulated at a frequency sufficiently slow compared to an imaging speed of the imaging unit 61, and thus the interference intensity may be calculated by the above-described algorithm from a temporal variation of the interference image obtained by the imaging unit 61.

Further, the phase lock may also be performed by rapidly reading the detection signal from any of pixels of the imaging unit 61 without being limited to monitoring of the interference intensity. In recent years, a frame rate exceeding 1 kHz has been realized through technical renovations of a CCD camera and a CMOS camera, and such a frame rate is sufficient for deriving phase information even in any one case of the first phase lock technique and the second phase lock technique.

Further, a liquid crystal element (for example, a liquid crystal lens) or a prism, of which the refractive index or the geometrical thickness is changed according to an applying voltage value, may be inserted to any one or both of the optical path of the first split light and the optical path of the second split light from the splitting to the combining in the interference optical system, and even in this case, it is possible to adjust the optical path difference between the optical path of the first split light and the optical path of the second split light from the splitting to the combining in the interference optical system.

INDUSTRIAL APPLICABILITY

On aspect of the present invention is possible to be used as the interference observation apparatus and the interference observation method which can easily acquire the interference image with a good image quality, and configure the apparatus at a low cost.

REFERENCE SIGNS LIST 1, 1A-1E; 2, 2A—interference observation apparatus, 10—light source, 11—lens, 12—beam splitter, 13—lens, 20, 21, 22—beam splitter (interference optical system), 31—sample holding table, 32—objective lens, 33—36—stage, 37—objective lens with correction collar, 41—reference mirror, 42—lens, 43—aberration correction plate, 44—piezo element, 45, 46—stage, 51—tube lens, 52—beam splitter, 54, 55—lens, 61—imaging unit, 62—photodetector, 71—image acquisition unit, 72—control unit, 73—numerical value display, 74—speaker, 81—sample holding table, 82—objective lens, 83—beam splitter, 84—fixed mirror, 85—optical path difference compensating plate, 91—reference mirror, 92—objective lens, 93—beam splitter, 94—piezo element, 95, 96—stage.

The invention claimed is:
1. An interference observation apparatus, comprising:
a light source configured to output incoherent light;
an interference optical system configured to split the light output from the light source into first split light and second split light, reflect or transmit the first split light by an observation object, and combine the first split light and the second split light to output combined light;
a light receiving unit configured to receive the combined light and output a detection signal;
an image acquisition unit configured to acquire an interference image on the basis of the detection signal; and
a controller configured to obtain an interference intensity of the combined light on the basis of the detection signal, and adjust the interference optical system to increase the interference intensity, wherein
the light receiving unit includes an image sensor configured to capture an image of the combined light and output a first detection signal, and a photodetector configured to receive the combined light and output a second detection signal,
the image acquisition unit is configured to acquire the interference image on the basis of the first detection signal,
the controller is configured to obtain the interference intensity on the basis of the second detection signal,
the controller is configured to adjust an optical path difference between the first split light and the second split light from the splitting to the combining in the interference optical system to increase the interference intensity,
the controller is configured to obtain a phase difference in accordance with the optical path difference in the interference optical system on the basis of the second detection signal, and repeatedly perform an ON period in which the optical path difference in the interference optical system is kept constant on the basis of the phase difference and an OFF period in which the optical path difference in the interference optical system is not kept constant so that the interference optical system is adjusted while intermittently performing the ON periods, and the image sensor is set such that a period of capturing the image of the combined light is included in the ON period.

2. The interference observation apparatus according to claim 1, wherein the controller is configured to adjust an optical axis of an optical element on any one or both of optical paths of the first split light and the second split light in the interference optical system to increase the interference intensity.

3. The interference observation apparatus according to claim 1, further comprising a display configured to display the interference intensity.

4. The interference observation apparatus according to claim 3, wherein the display is configured to display a temporal variation of the interference intensity as a graph.

5. The interference observation apparatus according to claim 3, wherein the display is configured to display the interference intensity as a numerical value.

6. The interference observation apparatus according to claim 3, wherein the display is configured to output the interference intensity as a sound.

7. The interference observation apparatus according to claim 1, wherein the interference optical system includes a Michelson interferometer or a Mach-Zehnder interferometer.

8. The interference observation apparatus according to claim 1, wherein the ON period is 1 msec or more and 3 sec or less.

9. The interference observation apparatus according to claim 1, wherein the OFF period is 30 msec or less.

10. An interference observation method, comprising:

splitting incoherent light output from a light source using an interference optical system into first split light and second split light, reflecting or transmitting the first split light by an observation object, and combining the first split light and the second split light to output combined light;

receiving the combined light using a light receiving unit and outputting a detection signal;

acquiring an interference image on the basis of the detection signal using an image acquisition unit; and obtaining an interference intensity of the combined light on the basis of the detection signal, and adjusting the interference optical system to increase the interference intensity, wherein the light receiving unit includes an image sensor configured to capture an image of the combined light and output a first detection signal, and a photodetector configured to receive the combined light and output a second detection signal, the image acquisition unit is configured to acquire the interference image on the basis of the first detection signal, the interference intensity is obtained on the basis of the second detection signal, an optical path difference between the first split light and the second split light from the splitting to the combining in the interference optical system is adjusted to increase the interference intensity, a phase difference in accordance with the optical path difference in the interference optical system is obtained on the basis of the second detection signal, an ON period in which the optical path difference in the interference optical system is kept constant on the basis of the phase difference and an OFF period in which the optical path difference in the interference optical system is not kept constant are repeatedly performed so that the interference optical system is adjusted while intermittently performing the ON periods, and a period of capturing the image of the combined light by the image sensor is set to be included in the ON period.

11. The interference observation method according to claim 10, wherein an optical axis of an optical element on any one or both of optical paths of the first split light and the second split light in the interference optical system is adjusted to increase the interference intensity.

12. The interference observation method according to claim 10, wherein the interference intensity is displayed using a display.

13. The interference observation method according to claim 12, wherein the display is configured to display a temporal variation of the interference intensity as a graph.

14. The interference observation method according to claim 12, wherein the display is configured to display the interference intensity as a numerical value.

15. The interference observation method according to claim 12, wherein the display is configured to output the interference intensity as a sound.

16. The interference observation method according to claim 10, wherein the interference optical system includes a Michelson interferometer or a Mach-Zehnder interferometer.

17. The interference observation method according to claim 10, wherein the ON period is 1 msec or more and 3 sec or less.

18. The interference observation method according to claim 10, wherein the OFF period is 30 msec or less.

19. The interference observation apparatus according to claim 1, wherein a target phase difference in each ON period is set to the same value at every cycle.

20. The interference observation method according to claim 10, wherein a target phase difference in each ON period is set to the same value at every cycle.

* * * * *